(12) United States Patent
Henderson et al.

(10) Patent No.: US 8,178,670 B2
(45) Date of Patent: May 15, 2012

(54) METHOD OF SYNTHESIZING TETRAHYDROBIOPTERIN

(75) Inventors: Mark Henderson, Larkspur, CA (US); Steven Jungles, Novato, CA (US); Gabriele Roidl, Erlinsbach (CH); Robert Baffi, Moraga, CA (US); Adriano Indolese, Möhlin (CH); Christian Müller, Weil am Rhein (DE); Philipp Schmidt, Lörrach (DE); Stefan Kaiser, Binningen (CH)

(73) Assignee: BioMarin Pharmaceutical Inc., Novato, CA (US)

( * ) Notice: Subject to any disclaimer, the term of this patent is extended or adjusted under 35 U.S.C. 154(b) by 206 days.

(21) Appl. No.: 12/349,479

(22) Filed: Jan. 6, 2009

(65) Prior Publication Data

US 2009/0198055 A1 Aug. 6, 2009

Related U.S. Application Data

(60) Provisional application No. 61/046,909, filed on Apr. 22, 2008, provisional application No. 61/019,528, filed on Jan. 7, 2008.

(51) Int. Cl.
*C07D 475/00* (2006.01)
(52) U.S. Cl. ........................................ 544/258
(58) Field of Classification Search .................... 544/258
See application file for complete search history.

(56) References Cited

U.S. PATENT DOCUMENTS

| | | | |
|---|---|---|---|
| 2,601,215 | A | 6/1952 | Waller et al. |
| 3,505,329 | A | 4/1970 | Weinstock |
| 4,540,783 | A | 9/1985 | Viscontini |
| 4,550,109 | A | 10/1985 | Folkers et al. |
| 4,587,340 | A | 5/1986 | Nichol et al. |
| 4,595,752 | A | 6/1986 | Azuma et al. |
| 4,649,197 | A | 3/1987 | Uchino et al. |
| 4,665,182 | A | 5/1987 | Nichol et al. |
| 4,701,455 | A | 10/1987 | Nichol et al. |
| 4,713,454 | A | 12/1987 | Sakai et al. |
| 4,937,342 | A | 6/1990 | Kurono et al. |
| 5,037,981 | A | 8/1991 | Kurono et al. |
| 5,043,446 | A | 8/1991 | Kikuchi et al. |
| 5,184,622 | A | 2/1993 | Tomura |
| 5,198,547 | A | 3/1993 | Bailey et al. |
| 5,350,851 | A | 9/1994 | Bailey et al. |
| 5,401,844 | A | 3/1995 | Ayling et al. |
| 5,698,408 | A | 12/1997 | Rokos |
| 6,544,994 | B2 | 4/2003 | Rabelink et al. |
| 7,361,759 | B2 | 4/2008 | Tazawa |
| 2006/0035900 | A1 | 2/2006 | Moser et al. |
| 2006/0040946 | A1 | 2/2006 | Oppenheimer et al. |
| 2006/0142573 | A1 | 6/2006 | Tazawa |
| 2006/0194808 | A1 | 8/2006 | Richardson et al. |
| 2006/0211701 | A1 | 9/2006 | Muntau-Heger et al. |
| 2007/0244322 | A1 | 10/2007 | Moser et al. |
| 2008/0090832 | A1 | 4/2008 | Oppenheimer et al. |

FOREIGN PATENT DOCUMENTS

| | | |
|---|---|---|
| CA | 2420374 | 2/2003 |
| CH | 500999 | 12/1970 |
| CH | 651755 | 10/1985 |
| EP | 0165595 | 12/1985 |
| EP | 0191335 | 8/1986 |
| EP | 0385336 | 9/1990 |
| JP | 58-83691 | 5/1983 |
| JP | 59-112987 | 6/1984 |
| JP | 59-186986 | 10/1984 |
| JP | 1-221380 | 9/1989 |
| JP | 2-31720 | 7/1990 |
| JP | 2-55434 | 11/1990 |
| JP | 3-32553 | 5/1991 |
| JP | 4-13357 | 3/1992 |
| JP | 5-86393 | 12/1993 |

(Continued)

OTHER PUBLICATIONS

Notice of Allowability, U.S. Appl. No. 10/579,106, mailed Feb. 5, 2010.

(Continued)

*Primary Examiner* — James O Wilson
*Assistant Examiner* — Douglas M Willis
(74) *Attorney, Agent, or Firm* — Jones Day (57) ABSTRACT

The present disclosure provides a method that efficiently produces (6R)-tetrahydrobiopterin of Formula I in high yield and purity. The method includes the step of hydrolyzing diacetylbiopterin to biopterin under basic conditions in a biphasic mixture comprising an organic phase and an aqueous phase. After substantially complete hydrolysis of diacetylbiopterin, the aqueous phase containing biopterin can be separated from the organic phase containing most of the organic impurities, which avoids the time-consuming step of isolating biopterin as a solid. The aqueous solution containing biopterin is stereoselectively hydrogenated to (6R)-tetrahydrobiopterin under basic conditions and high hydrogen pressure in the presence of a metal catalyst (e.g., a platinum catalyst). To improve the purification of an acid addition salt of (6R)-tetrahydrobiopterin (e.g., (6R)-tetrahydrobiopterin dihydrochloride), any residual salts (e.g., sodium salts) in the aqueous solution after the hydrogenation reaction can be removed by contacting the aqueous solution with an ion (e.g., cation) exchange resin or column. Alternatively, removal of residual salts from the aqueous solution can be omitted if an organic amine (e.g., diethylamine or triethylamine) rather than an inorganic base is used in the hydrolysis and/or hydrogenation reactions.

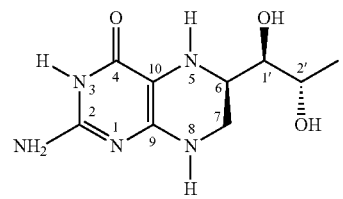

Formula I

26 Claims, 3 Drawing Sheets

FOREIGN PATENT DOCUMENTS

| | | |
|---|---|---|
| JP | 2567638 | 10/1996 |
| JP | 2567639 | 12/1996 |
| JP | 2575781 | 1/1997 |
| JP | 2611790 | 5/1997 |
| JP | 9-157270 | 6/1997 |
| JP | 2674707 | 11/1997 |
| JP | 2711828 | 2/1998 |
| JP | 2001-302665 | 10/2001 |
| WO | WO 94/21603 | 9/1994 |
| WO | WO 2005/065018 | 7/2005 |
| WO | WO 2006/070902 | 7/2006 |
| WO | WO 2006/112495 | 10/2006 |
| WO | WO 2006/118322 | 11/2006 |
| WO | WO 2008/089008 | 7/2008 |

OTHER PUBLICATIONS

Armarego et al., "The absolute configuration at C6 of natural 2-amino-6-[(1'R,2'S)-1',2'-dihydroxypropyl]-5,6,7,8-tetrahydropteridin-4(3H)-one (L-*erythro*-5,6,7,8-tetrahydrobiopterin)," *Aust. J. Chem.*, 35(4), 785-793 (1982).

Aizpurua et al., "Reaction of hindered trialkylsilyl esters and trialkylsilyl ethers with triphenylphosphine dibromide: Preparation of carboxylic acid bromides and alkyl bromides under mild neutral conditions," *J. Org. Chem.*, 51(25), 4941-4943 (1986).

Andrews et al., "A new synthesis of biopterin," *J. Chem. Soc.*, Section C, 6, 928-930 (1969).

Arnold, Phenylketonuria, eMedicine from webMD, Jun. 5, 2006, http://www.emedicine.com/PED/topic1787.htm.

Ashton et al., "Amino acid derivatives of β-cyclodextrin," *J. Org. Chem.*, 61(3), 903-908 (1996).

Bell et al., "The reduction of organic halogen compounds by sodium borohydride," *J. Org. Chem.*, 34, 3923-3926 (1969).

Blau et al., "Disorders of tetrahydrobiopterin and related biogenic amines" in *The metabolic and molecular bases of inherited disease*, 8th Ed., Scriver et al. Eds.New York, McGraw-Hill, 1725-1776 (2001).

Bradshaw et al., "Synthesis of the organic ligand of the molybdenum cofactor, in protected form," *J. Chem. Soc. Perkin Trans. 1*, 3239-3244 (2001).

Bredereck et al., "Darstellung und eigenschaften der amidacetale und aminalester," *Chem. Ber.*,101, 41-50 (1968).

Butenandt et al., "Isolierung von 2-amino-4-hydroxy-6-[1.2-dihydroxy-propyl-]pteridin," *Hoppe Seyler's Z Physiol. Chem.*, 311, 79-83 (1958) (with English summary).

Cha et al., "Isolation and characterization of limipterin (1-O-(L-erythro-biopterin-2-yl)-β-N-acetylglucosamine) and its 5,6,7,8-tetrahydro derivative from green sulfur bacterium chlorobium *limicola* f. thiosulfatophilum NCIB 8327," *Helv. Chim. Acta*, 78, 600-614 (1995).

Chaudhary et al., "4-Dimethylaminopyridine: an efficient and selective catalyst for the silyation of alcohols," *Tetrahedron Lett.*, 2, 99-102 (1979).

Choi et al., "Tetrahydrobiopter is released from and causes preferential death of catecholaminergic cells by oxidative stress," *Mol. Pharmacol.*, 58(3), 633-640 (2000).

Corey et al., "Protection of Hydroxyl groups as tert-butyldimethylsilyl derivatives," *J. Am. Chem. Soc.*, 94(17), 6190-9191 (1972).

Fernandez et al., "Total synthesis of L-biopterin from L-tartaric acid via 5-deoxy-L-arabinose," *J. Org. Chem.*, 61, 8698-8700 (1996).

Fernandez et al., "Optically pure dihydroxy γ-alkylated γ-butyrolactones starting from L-tartaric acid: Application to formal and total syntheses of natural products," *J. Org. Chem.*, 62(12), 4007-4014 (1997).

Forrest et al., "Pteridines from *drosophila*. III. Isolation and identification of three more pteridines," *J. Am. Chem. Soc.*, 77, 4865-4869 (1955).

Galley et al., "Circulating tetrahydrobiopterin concentrations in patients with septic shocks," *Brit. J. Anaesthesia*, 86(4), 578-580 (2001).

Green et al., *Protective groups in organic synthesis*, Wiley & Sons, 3rd Ed., 201-245 (1999).

Hanaya et al., "Selective N(3)-and-$O^4$-alkylation of L-biopterin: A convenient synthesis of 3- and $O^4$-methyl-L-biopterin and the versatile $N^2$-(N,N-dimethylaminomethylene)-N(3)-p-nitrophenethyl-protected-L-biopterin," *Pteridines*, 6(1), 1-7 (1995).

Hanessian et al.,"Reactions of carbohydrates with (halomethylene)dimethyliminium halides and related reagents. Synthesis of some chlorodeoxy sugars," *J. Org. Chem.*, 34(7), 2163-2170 (1969).

Hart et al., "Asymmetric synthesis of the carbapenam core from serine," *J. Org. Chem.*, 68(1), 187-190 (2003).

Hiroshi, "Synthesis of biopterin without the by-production of isobiopterin," *Bitamin*, 51(12), 544-545 (1977).

Hutchins et al., "Sodium borohydride in dimethyl sulfoxide or sulfolane. Convenient systems for selective reductions of primary, secondary, and certain tertiary halides and tosylates," *Tetrahedron Lett.*, 40, 3495-3498 (1969).

Kaiser et al., "80. Synthesis of biopterin from neopterin? The formation of pyrrolo[1,2-f]pteridins upon side-chain activation of neopterin," *Helv. Chim. Acta*, 70, 766-770 (1987).

Kang et al., "Synthesis of 2-ethylthio-6-(3-hydroxy-1,2-O-isopropylidenepropyl)pteridin-4(3H)-one," *Heterocycles*, 53(7), 1551-1557 (2000).

Kappel et al., "Synthese und Eigenschaften von Biopterin und Biopterin-Analogen," *Liebigs Ann. Chem.*, 1815-1825 (1984).

Khripak et al., "Transformations of some substituted 5-benzyl-1,2,4-triazoline-3-thione," *Chem. Heterocyclic Compounds*, 11, 740-742 (1975).

Kikuchi et al., "Synthesis of (−)-biopterin using (S)-ethyl lactate as a starting material," *Agric. Biol. Chem.*, 53(8), 2095-2100 (1989).

Kim et al., "Direct conversion of silyl ethers into alkyl bromides with boron tribromide," *J. Org. Chem.*, 53, 3111-3113 (1988).

Larock, *Comprehensive Organic Transformations*, Wiley VCH, 2nd Ed., 681-708 (1999).

Lin et al., "Chemical effects of $^{31}P(n,\gamma)^{32}P$ reaction in phosphate glass—A radiation chemical approach to hot atom chemistry," *Bull. Chem. Soc. Jpn.*, 48(12), 3450-3455 (1975).

Matsuura et al., "Highly stereoselective procedure for (6R)-tetrahydrobiopterin cofactor," *Chem. Lett.*, 13(5), 735-738 (1984).

Matsuura et al., "Stereochemistry of biopterin cofactor and facile methods for the determination of the stereochemistry of a biologically active 5,6,7,8-tetrahydropterin," *J. Biochem.*, 98(5), 1341-1348 (1985).

Matsuura et al., "Hydrogenation of biopterin and its analogues; application for the convenient procedure of biopterin cofactor and related 5,6,7,8-tetrahydropterin," *Heterocycles*, 23(12), 3115-3120 (1985).

Mattes et al., "Reactivity of t-butyldimethylsilyl ethers: A facile conversion into bromides," *Tetrahedron Lett.*, 28(15), 1697-1698 (1987).

Murata et al., "Novel region- and stereoselective synthesis of 6-substituted pteridines and naturally occurring L-erythro-biopterin," *Synthesis*, 303-308 (1992).

Mori et al., "A new synthesis of (−)-biopterin employing 5-deoxy-L-ribose as a key intermediate," *Liebigs Ann. Chem.*, 1989(12), 1267-1269 (1989).

Mori et al., "Synthesis of (−)-biopterin," *Liebigs Ann. Chem.*, 1989(10), 963-967 (1989).

National Institute of Neurological Disorders and Stroke, Disorder Index, Oct. 2006, http://www.ninds.nih.gov/disorders/disorder_index.htm?css—print.

Patterson et al., "The synthesis of a pteridine required for the growth of crithidia fasciculate," *J. Am. Chem. Soc.*, 78(58), 5868-5871 (1956).

Pellicciari et al., "Stereospecific synthesis of the enantiomers of nicotinylalaline, a neuroprotecting agent," *Tetrahedron Lett.*, 33, 3003-3004 (1992).

Ross et al., "Anodic oxidations. V. The Kolbe oxidation of phenylacetic acid and 1-methylcyclohexaneacetic acid at platinum and at carbon," *J. Org. Chem.*, 24, 2923-2927 (1969).

Russell et al., "Model studies related to the cofactor of the oxomolybdoenzymes Part 6: An improved synthesis of 6-substituted pterins from 2,4,5-triamino-6-hydroxy-pyrimidine and D-glucose," *Synlett*, 9, 711-712 (1992).

Russell et al., "Model studies related to the cofactor of the oxomolybdoenzymes Part 5: Synthesis of 6-alkenyl- and 6-alkynylpterins," *Tetrahedron Lett.*, 33(23), 3371-3374 (1992).

Schircks et al., "Eine neue, regiospezifische synthese von L-biopterin," *Helv. Chim. Acta*, 60(24), 211-215 (1977).

Schircks et al., "Herstellung von (6R,S)-5,6,7,8-tetrahydro-l-biopterin, 7,8-dehydro-l-biopterin, L-sepiapterin, deoxysepiapterin, (6R,S)-5,6-dehydrodeoxysepiapterin und 2'-deoxybiopterin)," *Helv. Chim. Acta*, 61(7), 2731-2738, (1978).

Schircks et al., "A new, regiospecific synthesis of L-biopterin," *Helv. Chim. Acta*, 68(6), 1639-1643 (1985).

Schircks Laboratories, "Tetrahydrobiopterin, Sales restrictions," (2006) http://www.schireks.com/tablets/tablets_info.htm.

Schisla et al., "Preparation of a zeolite-containing secondary alkyl sulfate surfactant composition," *Zeolites*, 16(2), 218-223 (1996).

Smith et al., *March's advanced organic chemistry, reactions mechanisms and structure*, Wiley & Sons, Inc., 5th Ed., 524-526 (2001).

Smith, "Medical news: General infectious disease," *MedPageToday* (Apr. 20, 2007).

Soyka et al., "Synthese und eigenschaften von 5,6-dihydro-6-(1,2,3-trihydroxypropyl)pteridinen: kovalente intromolekulare addukte," *Helv. Chim. Acta*, 73, 808-826 (1990).

Sugimoto et al., "The convenient syntheses of biopterin and its three optical isomers," *Bull. Chem. Soc. Jpn.*, 48(12), 3767-3768 (1975).

Sugimoto et al., "Chemistry and biological function of biopterin cofactor and related compounds," *J Synth. Org. Chem. Jpn.*, 46(6), 564-573 (1988).

Sugimoto et al., "Studies on biologically active pteridines. IV. Synthesis of several biopterin derivatives as an antigen in radioimmunoassay for biopterin," *Bull. Chem. Soc. Jpn.*, 53(8), 2344-2347 (1980) (with partial English translation).

Taylor et al., "An unequivocal total synthesis of L-erythro-biopterin," *J. Am. Chem. Soc.*, 96(21), 6781-6782 (1974).

Taylor et al., "Pteridines. XXXVII. A total synthesis of L-erythro-biopterin and some related 6-(polyhydroxyalkyl)pterins," *J. Am. Chem. Soc.*, 98(8), 2301-2307 (1976).

Tsai et al., "Pharmacology in autism," *Psychosomatic medicine*, 61, 651-665 (1999).

Viscontini et al., "Synthese und eigenschaften des L-erythro-2-amino-6-hydroxy-8-dihydroxypropyl-pteridins und des D-threo-2-amino-6-hydroxy-8-dihydroxypropyl-pteridins," *Helv. Chim. Acta*, 41, 108-113 (1958) (with partial English translation).

Viscontini et al., "Synthese des natürlichen D-neopterins und L-monapterins," *Helv. Chim. Acta*, 53, 1202-1207 (1970).

Viscontini et al., "Eine neue synthese von D, L-biopterin," *Helv. Chim. Acta*, 55(60), 574-579 (1972).

Viscontini et al., "The synthesis of L-biopterin" in *Biochemical and Clinical Aspects of Pteridines*, vol. 3, Pfleiderer Ed., Walter de Gruyter & Co., 19-33 (1984).

Zinner et al., "Die partielle veresterung von D-arabinose-mercaptalen mit sulfonsaurechloriden und eine einfache synthese der 5-desoxy-D-arabinose," *Chem. Ber.*, 92, 1618-1623 (1959).

Zinner et al., "Synthese und derivate der 2,5-didesoxy-D-ribose," *Chem. Ber.*, 92, 2893-2896 (1959).

Watabe, "Purification and characterization of tetrahydrofolate. Protein complex in bovine liver," *J. Biol. Chem.*, 253(19), 6673-6679 (1978).

Wikipedia, "Lithium chloride," http://en.eikipedia.org/wiki/Lithium_chloride, last modified, Nov. 19, 2007.

Office Action mailed Apr. 2, 2008, U.S. Appl. No. 10/990,316.
Office Action mailed Oct. 23, 2007, U.S. Appl. No. 10/990,316.
Office Action mailed Jun. 28, 2007, U.S. Appl. No. 10/990,316.
Office Action mailed Nov. 28, 2006, U.S. Appl. No. 10/990,316.
Office Action mailed Sep. 18, 2007, U.S. Appl. No. 11/066,255.
Office Action mailed Mar. 12, 2007, U.S. Appl. No. 11/066,255.
Notice of Allowance mailed Dec. 4, 2007, U.S. Appl. No. 11/066,255.
U.S. Appl. No. 60/520,767, Daniel Oppenheimer, filed Nov. 17, 2003.
U.S. Appl. No. 10/991,573, filed Nov. 17, 2004 (Daniel Oppenheimer).

METHOD OF SYNTHESIZING TETRAHYDROBIOPTERIN

CROSS-REFERENCE TO RELATED APPLICATIONS

The present application claims priority to and the benefit of U.S. Provisional Application No. 61/046,909, filed on Apr. 22, 2008, and U.S. Provisional Application No. 61/019,528, filed on Jan. 7, 2008, both of which are incorporated herein by reference in their entirety.

FIELD OF THE DISCLOSURE

The disclosure relates generally to production of sapropterin. Furthermore, the disclosure relates to an improved process for production of sapropterin suitable for large-scale production.

BACKGROUND

Sapropterin (also called tetrahydrobiopterin, or "BH4") is a naturally occurring alkaloid of the pterin family. The biologically active stereoisomer of sapropterin has the chemical structure shown in Formula I:

Formula I

Sapropterin can also exist in other tautomeric forms of the pyrimidine ring. The nomenclature of the bioactive stereoisomer of sapropterin is (6R)-2-amino-6-[(1R,2S)-1,2-dihydroxypropyl]-5,6,7,8-tetrahydro-4(1H)-pteridinone, or (6R)-L-erythro-tetrahydrobiopterin, or 6R-BH4.

The chemical synthesis of sapropterin is well known. Access to the molecule has been accomplished by a variety of methods, using different starting materials to produce both the pterin ring structure portion of the molecule as well as the specific side chain required for pharmacological effect. Methods of synthesizing sapropterin are disclosed in, for example, U.S. Pat. Nos. 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408; and 5,698,408; and published Canadian Patent Application No. 2,420,374.

Pterins are bicyclic compounds that include a pyrazine ring and a pyrimidine ring having a carbonyl oxygen and an amino group. Pterins function as cofactors in enzymatic catalysis. Sapropterin functions as a cofactor for a number of different enzymes, including phenylalanine hydroxylase (PAH), tyrosine 3-hydroxylase, tryptophan 5-hydroxylase, and all three isoforms of nitric oxide synthase (NOS). Sapropterin also is a growth factor for *Crithidia fasciculata*, has proliferative activity in haemopoietic cells, and acts as a self-protecting factor for nitric oxide toxicity. These and other cofactor and cellular functions of sapropterin, as well as disorders relating to sapropterin deficiency, are disclosed in Thony et al., *Biochem. J.*, 347:1-16 (2000). Disorders relating to sapropterin deficiency also are generally described in Blau et al., "Disorders of Tetrahydrobiopterin and Related Biogenic Amines," in *The Metabolic and Molecular Bases of Inherited Disease*, 8th Ed., pp. 1275-1776, McGraw-Hill Publishing Co. (New York, N.Y., 2001).

The present disclosure provides a more efficient synthesis of sapropterin.

SUMMARY

One aspect of the disclosure provides a method for synthesis of sapropterin, including the step of hydrolyzing diacetylbiopterin to biopterin under basic conditions in a biphasic mixture comprising an organic phase and an aqueous phase. The method can also include, after substantially complete hydrolysis of diacetylbiopterin, separating the aqueous phase containing biopterin from the organic phase, and then hydrogenating the biopterin in the aqueous solution to sapropterin. After hydrogenation of biopterin, residual salts (e.g., inorganic salts such as sodium salts) can be removed from the aqueous solution by contacting the aqueous solution with an ion (e.g., cation) exchange resin or column. The hydrolysis and hydrogenation reactions can also be conducted in the absence of an inorganic base to minimize or avoid the formation of inorganic salts such that contacting the aqueous solution with an ion exchange resin or column can be omitted.

Another aspect of the disclosure provides intermediates and products produced by the method described herein.

Further aspects and advantages of the present disclosure will be apparent to those of ordinary skill in the art from a review of the following detailed description, taken in conjunction with the drawings. While the synthetic method described herein is susceptible of embodiments in various forms, it is understood that the embodiments of the method provided herein are illustrative and are not intended to limit the disclosure to the specific embodiments described herein.

BRIEF DESCRIPTION OF THE DRAWINGS

To facilitate the understanding of the present disclosure, drawing figures are appended hereto.

DETAILED DESCRIPTION

As a solid, sapropterin can be isolated as an acid addition salt. Most commonly, sapropterin is isolated as a dihydrochloride salt, and it is in this form that sapropterin is most often provided in pharmacological formulations. However, sapropterin can also be isolated as other kinds of acid addition salts, including, but not limited to, salts of sulfuric acid, hydrobromic acid, or organic acids.

The synthetic method of Sakai, U.S. Pat. No. 4,713,454, has been employed to produce the compound of Formula I at a scale ranging from 1 kg to 6 kg for commercial purposes.

To enable larger-scale production of BH4, modifications can be made to the process according to Shiratori Pharmaceutical Co., Ltd., described in U.S. Pat. No. 7,361,759 and International Patent Publication WO 2006/070902. A modified process based on the Shiratori process is shown in Scheme I:

12
pure (6R)-L-erythro-BH₄ dihydrochloride

11
"crude" (6R)-BH₄ dihydrochloride

The synthetic method of Scheme I, however, remains inadequate for industrial scale production of sapropterin dihydrochloride, in large part because the method calls for isolation of a key intermediate, L-biopterin (compound 10), which involves long processing time. To make about 300 kg biopterin, the process of Scheme I requires on average 265 hours (11 days) to hydrolyze diacetylbiopterin and filter and dry biopterin, in part because biopterin precipitates from solution as fine-grained particles that are difficult to filter. For large-scale production (e.g., one metric ton) of sapropterin dihydrochloride by the process of Scheme I, about one-third of the total processing time would be spent performing the isolation of biopterin. In contrast, the whole hydrolysis step in certain embodiments of the present process, as exemplified by Example 4, takes only 24 hours (1 day) to produce about 155 kg biopterin because biopterin is not isolated as a solid or dried, but rather is collected in the aqueous phase and separated from organic impurities dissolved in the organic phase of the biphasic hydrolysis mixture. Moreover, solution handling rather than solid isolation streamlines the present process so that multiple batches of biopterin solution can be made simultaneously and held for further processing (including hydrogenation) later. By contrast, the 11 days required for the hydrolysis and biopterin isolation step (step 8) in the process of Scheme I makes it difficult to streamline the hydrolysis and hydrogenation steps.

The process of the present disclosure also significantly reduces the time required to perform the biopterin hydrogenation reaction. The hydrogenation reaction of the present process takes less than 23 hours (hydrogen uptake suggests the reaction is substantially complete within 10 hours), whereas the hydrogenation reaction of the Scheme I process takes 74 hours on average. The faster hydrogenation reaction of the present process compared to that of the Scheme I process may be attributed to various factors, including higher hydrogen pressure (50 bar vs. 5 mPa), higher temperature (25° C. vs. 0-5° C.), and higher purity of biopterin starting material (see below).

Figure 4:
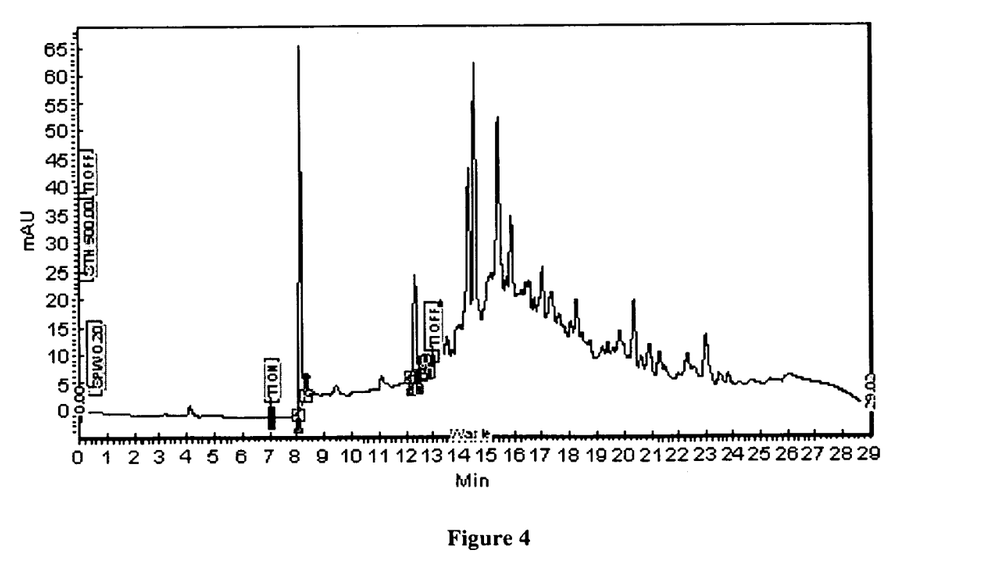
FIG. 4 is a chromatogram of a sample from the organic phase after overnight stirring of the hydrolysis reaction, showing biopterin and a small amount of the starting material, but mostly organic impurities.

Besides greatly reducing processing time for the hydrolysis and hydrogenation steps, the present process significantly improves the yield and purity of the products of both steps. The hydrolysis reaction of the present process produces biopterin in an average yield of 82% and an average purity of 92%, while the hydrolysis reaction (step 8) of the Scheme I process generates biopterin in an average yield of 60% and an average purity of 83% (as determined by the same analytical technique). The significantly lower yield of biopterin in the hydrolysis reaction of Scheme I may be due in part to elimination of the two hydroxyl groups from the BH4 side chain to form a propenyl side chain, or complete elimination of the side chain, under acidic reaction conditions at 60° C. The biopterin product of the present process has high purity by virtue of the fact that the aqueous phase of the biphasic reaction mixture contains biopterin absent any significant impurities (FIG. 2), while most of the organic byproducts and impurities of the hydrolysis reaction are removed with the organic phase (FIG. 4).

Further, the 64% average yield of "crude" (6R)-BH4 dihydrochloride after the hydrogenation step of the present process is significantly greater than the 54% average yield of crude (6R)-BH4 dihydrochloride (compound 11) after the hydrogenation step (step 9) of Scheme I. The lower yield of compound 11 in the Scheme I process compared to that of the present process is due in part to more incomplete hydrogenation (18% average amount of 7,8-dihydrobiopterin after termination of hydrogenation according to the process of Scheme I vs. 2% in the instant process) and a lower (6R)-BH4:(6S)-BH4 ratio (average of 8.5 according to the process of Scheme I vs. 10.5 in the instant process). The present process also provides pure (6R)-BH4 dihydrochloride in a slightly greater average yield (90%) after the final acidification/recrystallization step than step 10 of the Scheme I process (86%). Altogether, the hydrolysis and hydrogenation steps of the present process produce "crude" (6R)-BH4 dihydrochloride in a significantly greater average yield (53%) than steps 8 and 9 of the Scheme I process (32%), and the final three steps of the present process provide pure (6R)-BH4 dihydrochloride in a significantly greater average yield (48%) than steps 8, 9, and 10 of Scheme I (28%).

One aspect of the disclosure is a synthesis process (optionally including steps such as steps 1-7 in Scheme I, to yield diacetylbiopterin), wherein the synthesis of BH4 dihydrochloride (compound 12) is achieved without separate isolation or drying of solid biopterin (compound 10). Another aspect of the disclosure is a process by which material resulting from hydrolysis of diacetylbiopterin (compound 9) is hydrogenated without laborious work up procedures. In a further embodiment, any unhydrolyzed acyl groups on diacetylbiopterin are hydrolyzed under the conditions of hydrogenation. In another embodiment, the (6R) stereochemistry of BH4 is stereoselectively obtained via hydrogenation of biopterin.

The present disclosure provides an improved process for synthesizing sapropterin (including sapropterin dihydrochloride), including hydrolysis of diacetylbiopterin and hydrogenation of biopterin in commercial scale. The process includes the step of hydrolyzing diacetylbiopterin to biopterin under basic conditions in a biphasic mixture comprising an organic phase and an aqueous phase. After substantially complete hydrolysis of diacetylbiopterin, the process can include separating the aqueous phase containing biopterin from the organic phase, and then hydrogenating the biopterin in the separated aqueous phase to sapropterin. (6R)-sapropterin can be purified from an aqueous solution by methods known in the art; see, e.g., Matsuura et al., *Chem. Lett.*, 735 (1984), and U.S. Pat. Nos. 4,595,752 and 4,713,454.

The synthetic process described herein, and compounds produced by the process, encompass embodiments that can include one or more of the steps, elements, features, and/or components described herein (including those shown in Scheme I), or wherein one or more of the steps, elements, features, and/or components described herein can be substituted with substantially similar steps, elements, features, and/or components known in the art. For example, diacetylbiopterin (compound 9) can be synthesized according to Scheme I. As another example, LiCl can be substituted for $LiClO_4$ in step 6 in Scheme I.

In an embodiment, the pH of the aqueous phase of the diacetylbiopterin hydrolysis reaction is alkaline. In an embodiment, the pH of the aqueous phase is alkaline and about 12.2 or less, or about 12 or less. In certain embodiments, the pH of the aqueous phase of the hydrolysis reaction is in a range from about 10 to about 12.2, or from about 10.5 to about 12.2, or from about 11 to about 12.2, or from about 11.5 to about 12.2, or from about 11.8 to about 12. In a specific embodiment, the pH of the aqueous phase of the hydrolysis reaction is adjusted to a pH between about 11.5 and about 11.8 by addition of an inorganic base (e.g., sodium hydroxide) and/or an organic base (e.g., diethylamine or triethylamine). As the pH of the aqueous phase increases above about 12, the conversion rate may begin to decrease (it began to decrease above pH about 12.1 or 12.2 in one study). Moreover, as the pH of the aqueous phase of the hydrolysis reaction increases above about 12.2, the amount of impurities may increase. For example, in one study the yield of biopterin fell below 80% at about pH 12.2.

The ester moieties of diacetylbiopterin can be hydrolyzed under aqueous, basic conditions using any of a variety of basic reagents, including but not limited to phosphates (e.g., trisodium phosphate, disodium hydrogen phosphate, sodium dihydrogen phosphate, tripotassium phosphate, dipotassium hydrogen phosphate, potassium dihydrogen phosphate, and hydrates thereof, and combinations thereof); carbonates (e.g., sodium carbonate, sodium bicarbonate, potassium carbonate, potassium bicarbonate, and hydrates thereof, and combinations thereof); hydroxides (e.g., sodium hydroxide, potassium hydroxide, lithium hydroxide, and hydrates thereof, and combinations thereof); amines (e.g., ammonia, methylamine, ethylamine, dimethylamine, diethylamine, diisopropylamine, diethanolamine, trimethylamine, triethylamine, tripropylamine, diisopropylethylamine, cyclohexylamine, pyrrolidine, piperidine, morpholine, piperazine, imidazole, aniline, and indazole, and combinations thereof); ammonium hydroxides (e.g., ammonium hydroxide, tetramethylammonium hydroxide, tetraethylammonium hydroxide, tetrabutylammonium hydroxide, benzyltrimethylammonium hydroxide, and hydrates thereof, and combinations thereof); and combinations thereof. The quantity of basic reagent(s) used is optimized to attain an alkaline pH of the aqueous phase of the hydrolysis reaction, while limiting the amounts of residual salts present in the reaction mixture. The alkaline pH of the aqueous phase can be attained by using and/or adding basic reagent(s), including, without limitation, hydroxide(s), carbonate(s), phosphate(s), amine(s), ammonium hydroxide(s), and combinations thereof, as described herein.

In an embodiment, the aqueous phase of the diacetylbiopterin hydrolysis reaction is pH buffered. Because hydrolysis produces acetic acid, a pH buffering agent aids in maintaining a sufficiently alkaline pH for rapid hydrolysis. Without a buffer, the pH of the mixture may significantly decrease and hydrolysis may significantly slow down if an inorganic base is used at dilute concentration, until more base is added. This potential problem can be avoided by employing a large excess of base initially. Use of a buffer may also make it easier to set the pH of the hydrogenation mixture and keep it stable during the reaction, as the pH of the reaction mixture tends to rise since the product, tetrahydrobiopterin, is more basic than the starting material, biopterin. In certain embodiments, the pH of the aqueous phase of the diacetylbiopterin hydrolysis reaction, and/or the pH of the aqueous mixture of the biopterin hydrogenation reaction, is buffered through use and/or addition of phosphate reagent(s) (e.g., sodium dihydrogen phosphate, disodium hydrogen phosphate, trisodium phosphate, potassium dihydrogen phosphate, dipotassium hydrogen phosphate, and tripotassium phosphate, and combinations thereof), hydroxide(s) (e.g., sodium hydroxide, potassium hydroxide, and lithium hydroxide, and combinations thereof), carbonate(s) (e.g., sodium carbonate, sodium bicarbonate, potassium carbonate, and potassium bicarbonate, and combinations thereof), or combinations thereof.

In a further embodiment, ester hydrolysis is performed at a temperature of about 60° C. or less, or about 50° C. or less, or about 40° C. or less, to minimize or prevent the formation of elimination byproducts of biopterin. In certain embodiments, the temperature of the hydrolysis reaction is in a range from about 20° C. to about 60° C., or from about 20° C. to about 50° C., or from about 20° C. to about 40° C., or from about 25° C. to about 40° C., or from about 30° C. to about 40° C., or from about 30° C. to about 35° C., or from about 35° C. to about 40° C., or from about 40° C. to about 50° C., or from about 50° C. to about 60° C., to achieve substantially complete hydrolysis within a relatively short period of time, e.g., about 16 hours or less at about 40° C. or about 12 hours or less at about 30° C.

In another embodiment, the diacetylbiopterin hydrolysis reaction is conducted for a relatively short period of time, e.g., about twelve hours or less. In still another embodiment, the hydrolysis reaction is conducted overnight, which can total about 15 hours or less, or about 18 hours or less, or about 21 hours or less, or about 24 hours or less. The relatively short reaction time is advantageous for overall process time and efficient use of plant resources when conducting production campaigns.

The crude product of the oxidation step (corresponding to step 7 in Scheme I), containing a mixture of diacetylbiopterin, the two monoacetylbiopterins and biopterin, can be employed as the starting material in the hydrolysis reaction. The crude starting material of the hydrolysis reaction may contain, e.g., about 55% 1',2'-di-O-Ac-biopterin, about 25% 1'-O-Ac-biopterin, about 15% 2'-O-Ac-biopterin, and about 5% biopterin. In certain embodiments, the concentration of diacetylbiopterin "equivalent" (calculating any monoacetylbiopterins and any biopterin as diacetylbiopterin) in the aqueous phase of the hydrolysis reaction is up to about 300 mg/mL, or up to about 290 mg/mL, or up to about 280 mg/mL, or up to 270 mg/mL, or up to 260 mg/mL, or up to about 250 mg/mL, or up to about 240 mg/mL, or up to about 230 mg/mL, or up to about 220 mg/mL, or up to about 210 mg/mL, or up to about 200 mg/mL, or up to about 190 mg/mL, or up to about 180 mg/mL, or up to about 170 mg/mL, or up to about 160 mg/mL, or up to about 150 mg/mL. In certain embodiments, completion of the hydrolysis reaction results in a concentration of biopterin (assuming 100% yield) in the aqueous phase of up to about 220 mg/mL, or up to about 210 mg/mL, or up to about 200 mg/mL, or up to about 190 mg/mL, or up to about 180 mg/mL, or up to about 170 mg/mL, or up to about 160 mg/mL, or up to about 150 mg/mL, or up to about 140 mg/mL, or up to about 130 mg/mL, or up to about 120 mg/mL, or up to about 110 mg/mL, or up to about 100 mg/mL, or up to about 90 mg/mL, or up to about 80 mg/mL.

In certain embodiments, the concentration of diacetylbiopterin equivalent in the aqueous phase of the hydrolysis reaction is in a range from about 150 mg/mL to about 250 mg/mL (corresponding to a biopterin concentration in the aqueous phase from about 110 mg/mL to about 185 mg/mL assuming 100% yield of biopterin), or from about 160 mg/mL to about 240 mg/mL (corresponding to about 120 mg/mL to about 180 mg/mL biopterin), or from about 170 mg/mL to about 230 mg/mL (corresponding to about 125 mg/mL to about 170 mg/mL biopterin), or from about 180 mg/mL to about 220 mg/mL (corresponding to about 130 mg/mL to about 160 mg/mL biopterin), or from about 190 mg/mL to about 210 mg/mL (corresponding to about 140 mg/mL to about 155 mg/mL biopterin).

In other embodiments, the concentration of diacetylbiopterin equivalent in the aqueous phase of the hydrolysis reaction is in a range from about 150 mg/mL to about 300 mg/mL, or from about 200 mg/mL to about 300 mg/mL. 260 mg/mL diacetylbiopterin equivalent corresponds to a biopterin concentration in the aqueous phase of about 190 mg/mL assuming 100% yield of biopterin, 270 mg/mL diacetylbiopterin corresponds to about 200 mg/mL biopterin, 280 mg/mL diacetylbiopterin corresponds to about 205 mg/mL biopterin, 290 mg/mL diacetylbiopterin corresponds to about 215 mg/mL biopterin, and 300 mg/mL diacetylbiopterin corresponds to about 220 mg/mL biopterin.

Organic-soluble byproducts or impurities of the diacetylbiopterin hydrolysis reaction can be readily removed prior to hydrogenation of biopterin by use of water and a water-immiscible organic solvent in the hydrolysis reaction and separation of the aqueous phase from the organic phase after the reaction. Most of the organic impurities are removed via dissolution in the organic phase, while the aqueous phase contains crude biopterin of high purity (e.g., about 87% to 92% average purity). Another advantage with the use of an organic solvent in the hydrolysis reaction is that it allows for the optional use of an organic amine (e.g., methylamine, ethylamine, dimethylamine, diethylamine, diisopropylamine, diethanolamine, trimethylamine, triethylamine, tripropylamine, diisopropylethylamine, cyclohexylamine, piperidine, morpholine, and piperazine, and combinations thereof) as a base in the reaction. The water-immiscible organic solvent can be either denser or less dense than water.

Various kinds of water-immiscible organic solvents can be employed in the diacetylbiopterin hydrolysis reaction, including without limitation alcohols, ethers, aliphatic hydrocarbons, aromatic hydrocarbons, halogenated hydrocarbons, and combinations thereof. Non-limiting examples of water-immiscible organic solvents include: alcohols (e.g., butanol, pentanol, hexanol, heptanol, octanol, nonanol, decanol, and isomers thereof, and combinations thereof); ethers (e.g., diethylether, 1,4-dioxane, and 1,3-dioxane, and combinations thereof); aliphatic hydrocarbons (e.g., pentane, hexane, heptane, octane, nonane, decane, and isomers thereof, and combinations thereof); aromatic hydrocarbons (e.g., benzene, toluene, xylene, and isomers thereof, and combinations thereof); and halogenated hydrocarbons (e.g., dichloromethane, chloroform, dichloroethane, trichloroethane, and isomers thereof, and combinations thereof). In one embodiment, the biphasic mixture of the hydrolysis reaction comprises n-butanol (1-butanol).

Figure 1:
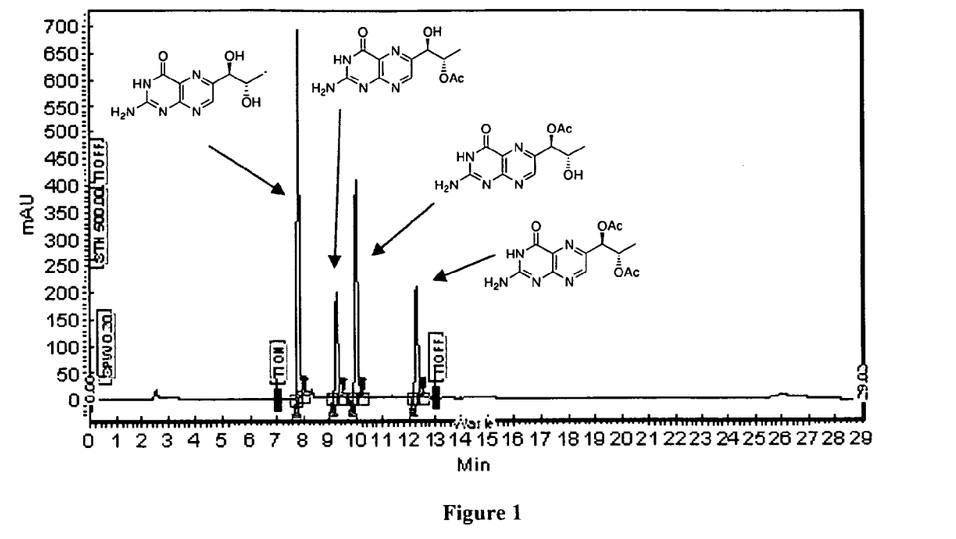
FIG. 1 illustrates a chromatogram of an initial aqueous-phase sample of the diacetylbiopterin hydrolysis reaction, showing the presence of diacetylbiopterin, as well as biopterin and two monoacetylbiopterin species.
Figure 2:
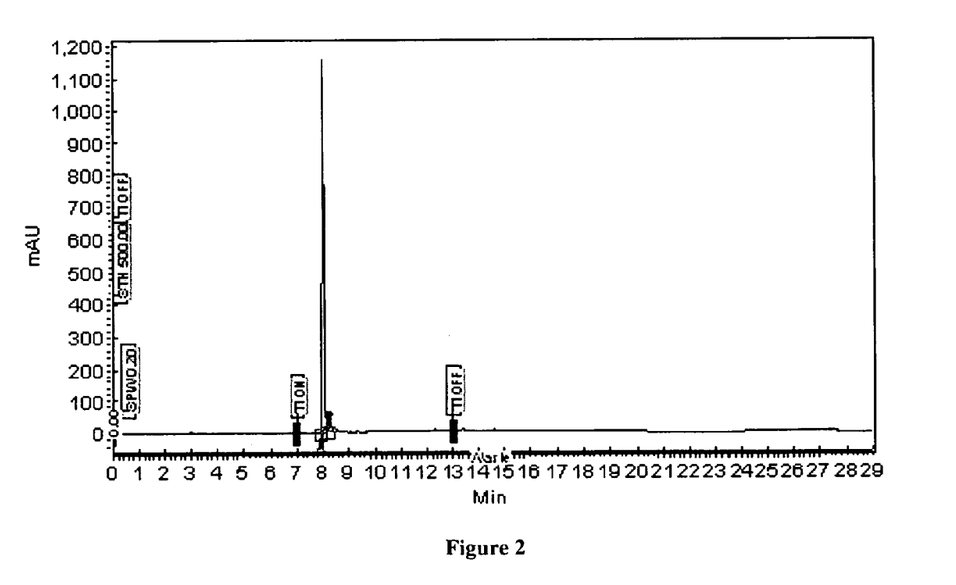
FIG. 2 is a chromatogram of a sample from the aqueous phase after overnight stirring of the hydrolysis reaction, showing the presence of only biopterin, absent any significant impurities.
Figure 3:
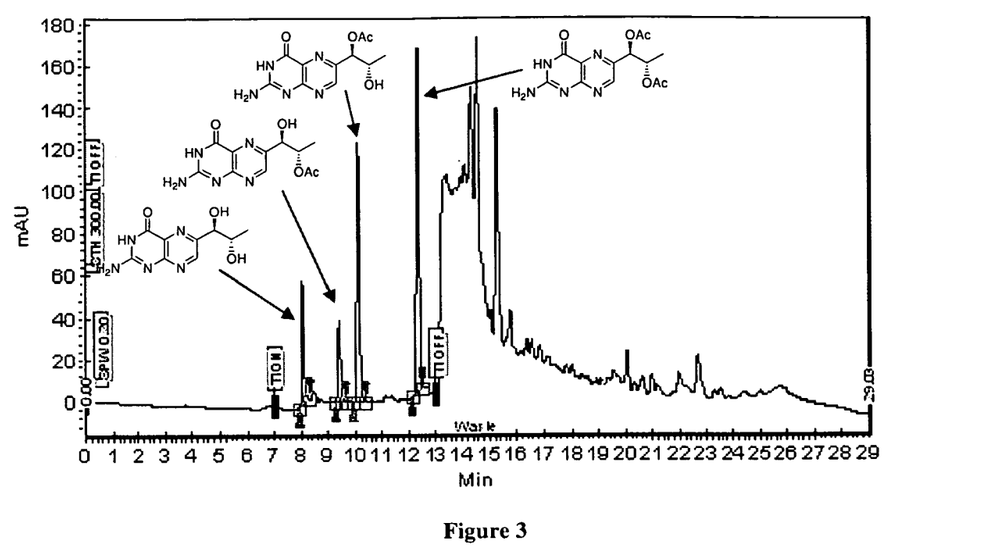
FIG. 3 displays a chromatogram of an initial organic-phase sample of the diacetylbiopterin hydrolysis reaction, showing the presence of the starting material and full and partial hydrolysis products, along with unidentified organic impurities.

FIGS. 1 to 4 illustrate the hydrolysis of diacetylbiopterin over time, and the separation of organic impurities from the desired product, biopterin, by their dissolution in the organic phase. The biopterin dissolved in the organic phase constitutes less than 2% of the total biopterin. FIG. 1 depicts a chromatogram of an initial sample from the aqueous phase of the diacetylbiopterin hydrolysis reaction, showing the presence of diacetylbiopterin, biopterin and two monoacetylbiopterin species. FIG. 2 is a chromatogram of a sample from the aqueous phase after the hydrolysis reaction is stirred overnight, showing the presence of only biopterin, absent any significant impurities. FIG. 3 displays a chromatogram of an initial sample from the organic phase of the hydrolysis reaction, showing the presence of the starting material and full and partial hydrolysis products, as well as unidentified organic impurities. FIG. 4 is a chromatogram of a sample from the organic phase after the hydrolysis reaction is stirred overnight, showing biopterin and a small amount of diacetylbiopterin, but mostly unidentified organic impurities in the organic phase.

In certain embodiments, the hydrolysis of diacetylbiopterin to form biopterin is performed in a mixture under basic conditions, using any of the inorganic bases, organic bases, and/or pH buffering agents described herein. In certain embodiments, the mixture is monophasic. In certain embodiments, the mixture is a monophasic aqueous mixture. In certain embodiments, after substantial completion of hydrolysis in a monophasic aqueous mixture, a water-immiscible organic solvent (e.g., n-butanol) is added to extract any impurities, byproducts and/or unreacted starting material into the organic layer from the aqueous mixture that contains the biopterin produced. In certain embodiments, the hydrolysis reaction mixture contains a water-immiscible organic solvent (e.g., n-butanol) and may optionally contain a sufficient amount of water to facilitate hydrolysis and/or dissolution of the starting material. In certain embodiments, after substantial completion of hydrolysis in an organic mixture that may optionally contain a sufficient amount of water, water is added to the organic mixture to recover biopterin into the aqueous layer, leaving behind any impurities, byproducts and/or unreacted starting material in the organic layer.

Hydrogenation of biopterin can be performed using a suitable metal catalyst, e.g., a platinum, palladium, or rhodium catalyst. In one embodiment, the hydrogenation is performed with a platinum catalyst. In an embodiment, the platinum catalyst is selected from platinum black, platinum oxide (including $PtO_2$ and hydrates thereof), platinum on carbon (including 10% Pt/C, 5% Pt/C, 3% Pt/C, 1% Pt/C, and 0.5% Pt/C), and platinum on alumina (including 5% Pt/alumina, 1% Pt/alumina, and 0.5% Pt/alumina). In one embodiment, the hydrogenation catalyst is platinum black or platinum oxide. Both platinum black and platinum oxide give a high percentage of conversion, but hydrogenation with Pt black can result in a higher ratio of (6R)-sapropterin to (6S)-sapropterin. If $PtO_2$ (Adam's catalyst) is employed, hydrogenation of the catalyst converts it to Pt black of fine particle size.

In an embodiment, the amount of the metal catalyst (also referred to herein as the catalyst load) used in the hydrogenation reaction is about 10 mol % or less based on the amount of diacetylbiopterin equivalent prior to the hydrolysis reaction or based on the amount of biopterin equivalent prior to the hydrogenation reaction. Efficient hydrogenation of biopterin is achieved with the use of about 10 mol % or less of hydrogenation catalyst. In certain embodiments, the amount of the hydrogenation catalyst used is about 8 mol % or less, or about 7 mol % or less, or about 6 mol % or less, or about 5 mol % or less, or about 4 mol % or less, based on the amount of diacetylbiopterin equivalent or biopterin equivalent. In certain embodiments, the amount of the hydrogenation catalyst used is in a range from about 2 to about 8 mol %, or from about 2 to about 7 mol %, or from about 2 to about 6 mol %, or from about 2 to about 5 mol %, or from about 2 to about 4 mol %, or from about 2 to about 3 mol %, or from about 2.2 to about 2.8 mol %, or from about 2.1 to about 2.6 mol %, based on the amount of diacetylbiopterin equivalent or biopterin equivalent.

In a further embodiment, the hydrogenation of biopterin is conducted in a pressure vessel under a hydrogen pressure in a range from about 14 bar to about 100 bar, or from about 14 bar to about 50 bar, or from about 50 bar to about 100 bar (1 bar is equivalent to 1 atm of pressure). In certain embodiments, the hydrogen pressure is in a range from about 14 to about 28 bar, or from about 20 to about 50 bar, or from about 25 to about 50 bar, or from about 30 to about 50 bar, or from about 35 to about 50 bar, or from about 40 to about 50 bar. In certain embodiments, the hydrogen pressure is about 100 bar, or about 50 bar, or about 35 bar, or about 28 bar, or about 21 bar, or about 14 bar. The hydrogenation of biopterin is diastereoselective, and greater 6R:6S diastereomeric ratios and conversions can be obtained at higher hydrogen pressure. For example, 6R:6S diastereomeric ratios around 20:1 may be attained by hydrogenating biopterin under a hydrogen pressure of about 100 bar, but commercial-scale hydrogenation under a hydrogen pressure greater than about 50 bar requires an expensive, specialized hydrogenation reactor.

In another embodiment, the hydrogenation of biopterin is performed at a temperature in a range from about 0° C. to about 40° C. or about 50° C. In certain embodiments, the hydrogenation is done at a temperature in a range from about 0° C. to about 20° C., or from about 0° C. to about 10° C., or from about 0° C. to about 5° C. In other embodiments, the hydrogenation reaction is conducted at a temperature in a range from about 20° C. to about 50° C., or from about 20° C. to about 40° C., or from about 25° C. to about 40° C., or from about 30° C. to about 40° C., or from about 20° C. to about 30° C., or from about 25° C. to about 35° C., or from about 25° C. to about 30° C., or from about 30° C. to about 35° C., or from about 35° C. to about 40° C., or from about 40° C. to about 50° C. In certain embodiments, hydrogenation is conducted at about 25° C. or about 30° C. Higher 6R:6S diastereomeric ratios may be obtained at lower temperature (down to about 0° C.), but hydrogenation at lower temperature may decrease the reaction rate and conversion and may require a specialized hydrogenation vessel. Hydrogenation at higher temperature, up to about 40° C. (or potentially up to about 50° C.), proceeds at a faster rate and gives greater conversion without significant decrease in 6R:6S diastereoselectivity.

In yet another embodiment, the pH of the aqueous mixture, if the aqueous phase is separated from the organic phase after the hydrolysis reaction and collected, or the pH of the aqueous phase of a biphasic mixture, in the hydrogenation reaction is alkaline. In certain embodiments, the pH of the biopterin-containing aqueous mixture or aqueous phase of the hydrogenation reaction is in a range from about 10 to about 12.5, or from about 10 to about 12, or from about 10.5 to about 12.5, or from about 10.5 to about 12, or from about 11 to about 12.5, or from about 11 to about 12, or from about 11.5 to about 12.5, or from about 11.5 to about 12. Besides promoting solubility of biopterin in the aqueous mixture or aqueous phase, a relatively high pH improves 6R:6S diastereoselectivity and promotes hydrolysis of any residual diacetylbiopterin or monoacetylbiopterins.

The pH of the aqueous mixture or the aqueous phase of the hydrogenation reaction can be made alkaline through use of a basic inorganic reagent and/or a basic organic reagent. Non-limiting examples of basic reagents that can be employed to attain an alkaline pH of the aqueous mixture or aqueous phase of the hydrogenation reaction include phosphates (e.g., trisodium phosphate, disodium hydrogen phosphate, sodium dihydrogen phosphate, tripotassium phosphate, dipotassium hydrogen phosphate, potassium dihydrogen phosphate, and hydrates thereof, and combinations thereof); carbonates (e.g., sodium carbonate, sodium bicarbonate, potassium carbonate, potassium bicarbonate, and hydrates thereof, and combinations thereof); hydroxides (e.g., sodium hydroxide, potassium hydroxide, lithium hydroxide, and hydrates thereof, and combinations thereof); amines (e.g., ammonia, methylamine, ethylamine, dimethylamine, diethylamine, diisopropylamine, diethanolamine, trimethylamine, triethylamine, tripropylamine, diisopropylethylamine, pyrrolidine, cyclohexylamine, piperidine, morpholine, piperazine, imidazole, aniline, and indazole, and combinations thereof); ammonium hydroxides (e.g., ammonium hydroxide, tetramethylammonium hydroxide, tetraethylammonium hydroxide, tetrabutylammonium hydroxide, benzyltrimethylammonium hydroxide, and hydrates thereof, and combinations thereof). In an embodiment, the pH of the aqueous mixture or aqueous phase of the hydrogenation reaction is raised to and/or maintained at a pH of at least about 10 or 11 by use and/or addition of an organic amine (e.g., diethylamine or triethylamine).

In certain embodiments, the concentration of biopterin "equivalent" (calculating any diacetylbiopterin and any monoacetylbiopterins as biopterin) in the aqueous mixture or the aqueous phase of the hydrogenation reaction is up to about 5%, 6%, 7%, 8%, 9%, 10%, 11%, 12%, 13%, 14%, or up to about 15% w/w. In further embodiments, the concentration of biopterin equivalent in the aqueous mixture or the aqueous phase of the hydrogenation reaction is in a range from about 1% to about 15% w/w, or from about 1% to about 10% w/w, or from about 2% to about 10% w/w, or from about 2% to about 8% w/w, or from about 2% to about 7% w/w, or from about 3% to about 7% w/w, or from about 4% to about 6% w/w.

In another embodiment, a separate diacetylbiopterin hydrolysis step is omitted, and hydrolysis of the ester groups and hydrogenation of the pyrazine ring are performed in one step under any of the conditions for the hydrogenation reaction described herein. The acetate ester groups are hydrolyzed under alkaline conditions (e.g., pH in a range from about 10 to about 12.5) for the hydrogenation reaction. The crude product of the oxidation step (corresponding to step 7 in Scheme I) can be used as the starting material in the one-pot hydrolysis/hydrogenation reaction. The one-pot reaction can be conducted in a biphasic mixture comprising an alkaline aqueous phase and an organic phase. Alternatively, the one-pot reaction can be conducted in a monophasic alkaline aqueous mixture, and after substantial completion of both hydrolysis and hydrogenation, a water-immiscible organic solvent can be added to the mixture to extract any organic byproducts, impurities and/or unreacted starting material into the organic layer, leaving behind the desired product, tetrahydrobiopterin, in the aqueous layer, which can be separated from the organic layer and collected. Whether conducted in a mono- or bi-phasic alkaline aqueous mixture, any of the inorganic bases, organic bases, and/or pH buffering agents described herein can be employed in the one-pot hydrolysis/hydrogenation reaction, and the reaction can be worked up in any manner as described herein. The one-pot hydrolysis/hydrogenation reaction can provide tetrahydrobiopterin in high yield (e.g., >80%) and high 6R:6S diastereoselectivity (e.g., >8:1).

The synthetic method described herein produces sapropterin, and/or acid addition salts of sapropterin (e.g., sapropterin dihydrochloride) after acidification of sapropterin, in high 6R:6S diastereomeric selectivity. In certain embodiments, the method produces sapropterin or acid addition salts thereof having a 6R:6S diastereoselectivity of at least about 7, 7.5, 8, 8.5, 9, 9.5, 10, 10.5, 11, 11.5, 12, 12.5, 13, 13.5, 14, 14.5, or at least about 15. Moreover, the method described herein produces (6R)-sapropterin in high yield. In certain embodiments, the hydrogenation reaction of the present method produces (6R)-sapropterin in a yield of at least about 60%, 65%, 70%, 75%, 80%, 85% or at least about 90%.

In certain embodiments, diacetylbiopterin (compound 9) is dissolved in an optionally buffered aqueous phase, whose pH is maintained between about 11 and about 12.2 or between about 11.5 and about 12.2, in the presence of at least one basic reagent (e.g., a basic inorganic reagent and/or a basic organic reagent); a water-immiscible organic solvent is also used, to form a biphasic mixture. The mixture is stirred at a temperature in a range from about 20° C. to about 40° C. until hydrolysis of the two acetate esters is substantially complete (e.g., the amount of any diacetylbiopterin and any monoacetylbiopterins totals ≦about 5% or about 10%) according to any of various analytical techniques, such as TLC, LC-MS or HPLC. Hydrogenation of the resulting mixture, after optional filtration (e.g., through celite), under a hydrogen pressure in a range from about 14 bar to about 50 bar and at a temperature in a range from about 0° C. to about 40° C. using a platinum catalyst (e.g., platinum black or platinum oxide), followed by separation of the aqueous phase from the organic phase, filtration of the aqueous phase through suitable media (e.g., celite and/or ion exchange resin) to remove any residual platinum catalyst and/or any residual salts, and acidification of the aqueous filtrate with HCl (alternatively, the separation, filtration and acidification can be performed in any order), produce sapropterin dihydrochloride in high 6R:6S diastereoselectivity (e.g., at least about 8:1 or 9:1) and high yield (e.g., about 65% to about 80%). In alternative embodiments, the organic and aqueous phases of the hydrolysis reaction are allowed to settle, the aqueous phase containing biopterin is separated from the organic phase containing organic impurities, and the aqueous phase is optionally filtered (e.g., through a celite pad or a filter aid, such as Vitacel FAC 200) (alternatively, the biphasic mixture can be filtered prior to separation of the aqueous phase), subjected to hydrogenation and worked up as described above to provide (6R)-sapropterin dihydrochloride in high diastereoselectivity and high yield.

Removal of any residual salts (e.g., inorganic salts) from the aqueous solution prior to the final acidification and purification step (corresponding to step 10 of Scheme I) can significantly improve the purity of the BH4 acid addition salt (e.g., (6R)-BH4 dihydrochloride) final product, e.g., by reducing or minimizing the salt content in the final crystallization mixture. The amount of salts (including inorganic salts) can be reduced, or their formation can be avoided, by various means, such as hydrolysis in the absence of a pH buffering agent, precipitation of salts before hydrogenation, contact with an ion exchange resin or column after hydrogenation, and hydrolysis and/or hydrogenation in the absence of an inorganic base.

In one embodiment, the amount of inorganic salts generated is reduced, or their generation is avoided, by conducting the diacetylbiopterin hydrolysis reaction in the absence of an inorganic base (e.g., sodium hydroxide) and/or in the absence of an inorganic pH buffering agent (e.g., a phosphate buffer). The pH of the aqueous phase of the hydrolysis reaction can be made alkaline by using an organic base (e.g., an organic amine, such as diethylamine or triethylamine) rather than an inorganic base and/or an inorganic pH buffer.

In another embodiment, the amount of inorganic salts in the biopterin-containing aqueous phase or aqueous solution is reduced by precipitating salts before hydrogenation. In one embodiment, after hydrolysis and prior to phase separation, the biphasic mixture is cooled to a lower temperature (e.g., from about 0° C. to about 5° C.) to induce precipitation of inorganic salts. The cooled mixture can be filtered to remove the precipitated salts. In another embodiment, after hydrolysis the aqueous phase is separated from the organic phase, the collected aqueous phase is cooled to a lower temperature (e.g., from about 0° C. to about 5° C.), and the cooled mixture is filtered to remove the precipitated salts. Besides inorganic salts, however, biopterin may also precipitate upon cooling of the aqueous mixture, which may decrease the yield of biopterin.

In a further embodiment, any residual salts (including inorganic salts) in the aqueous solution after hydrogenation and workup are removed by contacting the solution with an ion exchange resin or column. After hydrolysis, hydrogenation and workup (including filtration to remove the metal catalyst and separation of the aqueous phase from the organic phase if the phases were not separated prior to hydrogenation), the pH of the resulting aqueous solution is raised to and/or maintained at a pH of at least about 10 or 11 in preparation for removal of residual salts from the aqueous solution. In certain embodiments, the pH of the aqueous solution is raised to and/or maintained in a range from about 10 to about 12, or from about 10.5 to about 12, or from about 11 to about 12, or from about 11.5 to about 12, or from about 11.8 to about 12. An alkaline pH can be attained by addition of a basic inorganic reagent (such as an inorganic phosphate, carbonate and/or hydroxide, e.g., sodium hydroxide) and/or a basic organic reagent (such as an organic amine and/or organic ammonium hydroxide, e.g., triethylamine) in a manner that minimizes the formation of inorganic (e.g., sodium) salts. In one embodiment, the pH of the aqueous solution is raised to and/or maintained at a pH of at least about 10 or 11 by addition of an organic amine (e.g., diethylamine or triethylamine).

In an embodiment, any residual salts (e.g., sodium salts) are removed from the aqueous solution having a pH at least about 10 or 11 by contacting the aqueous solution with an ion exchange resin (e.g., a cation exchange resin), such as by batch (e.g., sequential) addition of a cation exchange resin, or by passing the aqueous solution over a cation exchange resin. Alternatively, any residual salts can be removed from the alkaline aqueous solution by running it through an ion (e.g., cation) exchange column. In an embodiment, while the aqueous solution is contacted with an ion (e.g., cation) exchange resin or column, the pH of the solution is maintained at a pH at least about 10 or 11 by addition of a suitable base (such as an organic amine, e.g., diethylamine or triethylamine), if necessary, to facilitate the resin or column taking up residual salts (e.g., $Na^+$).

The ion (e.g., cation) exchange resin or column can be washed with an aqueous solution containing an organic amine (e.g., diethylamine or triethylamine), to recover any sapropterin remaining on the resin or column. An advantage of washing the ion exchange resin or column with a mixture of water and an organic amine (e.g., water and triethylamine in a ratio, e.g., from about 3:1 to about 5:1), rather than washing with deionised water, is avoiding extraction of sodium from the resin or column. After the removal of any residual salts from the sapropterin-containing aqueous solution, the resulting filtrate can be acidified to produce an acid addition (e.g., hydrochloride) salt of sapropterin. Another advantage of using triethylamine to maintain the alkalinity of the aqueous solution and/or to recover any remaining BH4 from the ion exchange resin or column is that if BH4 is acidified with HCl and BH4 dihydrochloride is recrystallized from ethanol, triethylamine hydrochloride is much more soluble in ethanol than BH4 dihydrochloride and thus is readily separated from BH4 dihydrochloride by filtration.

In still another embodiment, an inorganic base is not used in any of the final three steps of hydrolysis, hydrogenation, and purification of (6R)-BH4 or acid addition salts thereof. By employing ammonia or an organic base (e.g., an organic amine) rather than an inorganic base in the hydrolysis and/or hydrogenation reactions, the amount of inorganic salts is minimized, or their formation is avoided, such that removal of any inorganic salts from the biopterin- or BH4-containing aqueous solution (e.g., by contacting the aqueous solution with an ion exchange resin or column after hydrogenation) can be avoided, as shown in the following set of embodiments.

In one set of embodiments of the method for preparing (6R)-BH4 dihydrochloride, the diacetylbiopterin hydrolysis reaction is conducted using an organic amine (e.g., diethylamine) in a biphasic mixture of water and a water-immiscible organic solvent (e.g., n-butanol), wherein the pH of the aqueous phase is at least about 10 or 11. The mixture is stirred at a temperature in a range from about 20° C. to about 40° C. until the hydrolysis reaction is substantially complete (e.g., the amount of diacetylbiopterin and monoacetylbiopterins totals ≦about 5% or 10%). The aqueous and organic phases are allowed to separate, the aqueous phase is collected, and the organic phase is optionally mixed with additional water to transfer any biopterin species remaining in the organic phase to the aqueous phase. The aqueous phase is optionally filtered, e.g., through a celite pad or a filter aid (e.g., Vitacel FAC 200). The concentration of biopterin in the aqueous solution is adjusted to ≦about 15% w/w, or ≦about 10% w/w, or ≦about 5% w/w by addition of water if necessary, and the pH of the solution is raised to at least about 10 or 11 by addition of an organic amine (e.g., triethylamine) if necessary. The mixture is stirred in the presence of a platinum catalyst (e.g., platinum black or platinum oxide) at a temperature in a range from about 20° C. to about 40° C. and under a hydrogen pressure in a range from about 20 bar to about 50 bar, until the hydrogenation reaction is substantially complete (e.g., the amount of biopterin and 7,8-dihydrobiopterin totals ≦about 5% or 10%). The mixture is filtered through a suitable medium (e.g., celite), the platinum catalyst is optionally recovered for recycling, and the filtrate is acidified to a pH of ≦about 4, 3, 2, or 1 by addition of HCl. The solution is concentrated under reduced pressure (e.g., ≦about 200-500 mbar) and at an elevated temperature in a range from about 40° C. to about 70° C. HCl is optionally added to the concentrated solution, and seed crystals of (6R)-BH4 dihydrochloride are optionally added to induce crystallization. After optional crystallization of (6R)-BH4 dihydrochloride, the mixture is optionally concentrated under reduced pressure (e.g., ≦about 200-500 mbar) and at an elevated temperature in a range from about 40° C. to about 70° C. To the concentrated mixture is optionally added an organic solvent (e.g., ethanol or n-butanol, or a combination thereof), and the resulting mixture is optionally stirred at an elevated temperature in a range from about 40° C. to about 70° C. and then optionally cooled to a temperature in a range from about 0° C. to about 40° C. to promote crystallization, and the resulting solid is optionally filtered. The filtered solid is optionally dissolved in water, and the resulting mixture is optionally stirred with activated charcoal at a temperature in a range from about 20° C. to about 40° C. to reduce colorization. The mixture is optionally filtered, and HCl is optionally added to the filtrate. For final purification of (6R)-BH4 dihydrochloride, the BH4-containing solution acidified by addition of HCl is concentrated under reduced pressure (e.g., ≦about 200-500 mbar) and at an elevated temperature in a range from about 30° C. to about 70° C. An organic solvent (e.g., n-butanol) is optionally added to the concentrated solution, and the resulting mixture is concentrated under reduced pressure (e.g., ≦about 200-500 mbar) and at an elevated temperature in a range from about 30° C. to about 70° C. to azeotropically remove residual water from the mixture. An organic solvent (e.g., ethanol) suitable for crystallization of (6R)-BH4 dihydrochloride is added to the concentrated mixture. The resulting mixture is stirred at an elevated temperature in a range from about 40° C. to about 70° C. and then is cooled, optionally with stirring, to a temperature in a range from about 0° C. to about 40° C., and is optionally seeded with seed crystals of (6R)-BH4 dihydrochloride, to facilitate crystallization. The crystallized product is filtered and optionally washed with an optionally warm organic solvent (e.g., ethanol). Drying of the filtered crystals optionally under reduced pressure (e.g., ≦about 200-500 mbar) and optionally at an elevated temperature (e.g., from about 40° C. to about 70° C.) provides pure (6R)-BH4 dihydrochloride.

In certain embodiments, provided herein is a method of preparing biopterin, comprising hydrolyzing diacetylbiopterin to biopterin in the presence of a base in a biphasic mixture, which comprises an aqueous phase and an organic phase containing a water-immiscible organic solvent, wherein the aqueous phase has a pH of at least about 10. In certain embodiments, the aqueous phase has a pH of at least about 11. In certain embodiments, the base is an amine. In certain embodiments, the base is diethylamine. In certain embodiments, the water-immiscible organic solvent is an alcohol. In certain embodiments, the water-immiscible organic solvent is n-butanol. In certain embodiments, the hydrolysis is carried out at a temperature from about 20° C. to about 50° C. In certain embodiments, the hydrolysis reaction is carried out at about 40° C. In certain embodiments, the concentration of diacetylbiopterin in the aqueous phase is from about 150 mg/mL to about 300 mg/mL.

In certain embodiments, the methods provided herein further comprise recovering biopterin from the hydrolysis reaction mixture, comprising allowing the aqueous phase and the organic phase to separate after the hydrolysis of diacetylbiopterin is substantially complete, and collecting the aqueous phase. In certain embodiments, the methods provided herein optionally comprise extracting the organic phase one or more times with water to recover any biopterin remaining in the organic phase, which comprises mixing the organic phase with a predetermined volume of water to form a mixture, allowing the aqueous phase and the organic phase of the mixture to separate, and collecting the aqueous phase.

In certain embodiments, the methods provided herein further comprise adding a base to the collected aqueous phase to raise the pH of the resulting aqueous mixture to at least about 10. In certain embodiments, the pH of the aqueous mixture is raised to at least about 11. In certain embodiments, the base used to adjust the pH of the collected aqueous phase is an amine. In certain embodiments, the base used to adjust the pH of the collected aqueous phase is triethylamine.

In certain embodiments, the methods further comprise hydrogenating biopterin in the aqueous mixture to tetrahydrobiopterin in the presence of a metal catalyst under a hydrogen pressure in a range from about 14 bar to about 100 bar. In certain embodiments, the hydrogenation reaction is performed at a hydrogen pressure from about 20 bar to about 50 bar. In certain embodiments, the hydrogenation reaction is performed at a hydrogen pressure of about 50 bar. In certain embodiments, the metal catalyst is a platinum catalyst. In certain embodiments, the metal catalyst is platinum black. In certain embodiments, the amount of the metal catalyst is in a range from about 2 mol % to about 8 mol % based on the amount of diacetylbiopterin prior to hydrolyzing diacetylbiopterin or based on the amount of biopterin prior to hydrogenating biopterin. In certain embodiments, the hydrogenation is performed at a temperature from about 0° C. to about 40° C. In certain embodiments, the hydrogenation is performed at a temperature from about 20° C. to about 30° C. In certain embodiments, the concentration of biopterin in the aqueous mixture of the hydrogenation reaction is from about 2% w/w to about 8% w/w. In certain embodiments, tetrahydrobiopterin is formed in a 6R:6S diastereomeric ratio of at least about 7:1. In certain embodiments, tetrahydrobiopterin is formed in a 6R:6S diastereomeric ratio of at least about 10:1.

In certain embodiments, the methods provided herein further comprise, after the hydrogenation of biopterin is substantially complete, filtering the aqueous mixture to remove the metal catalyst. In certain embodiments, the methods provided herein further comprise adding hydrochloric acid to the filtered aqueous mixture to lower the pH of the mixture to about 3 or lower. In certain embodiments, the pH of the aqueous mixture is lowered to about 1 or lower.

In certain embodiments, the methods provided herein further comprise concentrating the aqueous mixture under reduced pressure to remove water to form a first concentrated mixture. In certain embodiments, the aqueous mixture is concentrated at a temperature from about 30° C. to about 70° C.

In certain embodiments, the methods provided herein further comprise adding an organic solvent to the first concentrated mixture and concentrating the resulting mixture under reduced pressure to remove residual water to form a second concentrated mixture. In certain embodiments, the organic solvent is 1-butanol. In certain embodiments, the mixture is concentrated at a temperature from about 30° C. to about 70° C.

In certain embodiments, the methods provided herein further comprise adding an organic solvent to the first concentrated mixture or the second concentrated mixture, heating the resulting mixture to a temperature from about 40° C. to about 70° C., cooling the mixture to a temperature from about 0° C. to about 40° C., optionally adding seed crystals of (6R)-L-erythro-tetrahydrobiopterin dihydrochloride to the mixture to facilitate crystallization, and filtering the mixture to isolate (6R)-L-erythro-tetrahydrobiopterin dihydrochloride. In certain embodiments, the organic solvent is ethanol. In certain embodiments, the (6R)-L-erythro-tetrahydrobiopterin dihydrochloride isolated is in a crystalline form designated polymorph B.

In certain embodiments, provided herein is a method of preparing tetrahydrobiopterin, comprising:
  hydrolyzing diacetylbiopterin to biopterin in the presence of base in a biphasic mixture, which comprises an aqueous phase containing water and an organic phase containing a water-immiscible organic solvent, wherein the aqueous phase has a pH of at least about 10;
  optionally allowing the aqueous phase and the organic phase to separate after the hydrolysis of diacetylbiopterin is substantially complete and optionally collecting the aqueous phase as an aqueous mixture; and
  hydrogenating the biopterin in the aqueous mixture or the aqueous phase of the biphasic mixture, wherein the aqueous mixture or the aqueous phase has a pH of at least about 10, to tetrahydrobiopterin in the presence of a metal catalyst under a hydrogen pressure from about 14 bar to about 100 bar.

In one embodiment, the method further comprises recovering the biopterin from the reaction mixture after substantial completion of the hydrolysis reaction, which comprises allowing the aqueous phase and the organic phase of the reaction mixture to separate after the hydrolysis of diacetylbiopterin is substantially complete, and collecting the aqueous phase. In another embodiment, the method optionally comprises extracting the separated organic phase one or more times with water to recover any biopterin remaining in the organic phase, which comprises mixing the organic phase with a predetermined volume of water to form a mixture, allowing the aqueous phase and the organic phase of the mixture to separate, and collecting the aqueous phase. In yet another embodiment, the method further comprises adding a base to the collected aqueous phase to raise the pH of the aqueous mixture to at least about 10 prior to the hydrogenation. In yet another embodiment, the method further comprises filtering the reaction mixture after the hydrogenation of biopterin is substantially complete to remove the metal catalyst. In yet another embodiment, the method further comprises adding hydrochloric acid to the filtered aqueous mixture to lower the pH of the mixture to no greater than about 3. In yet another embodiment, the method further comprises concentrating the aqueous mixture under reduced pressure to remove water to form a first concentrated mixture. In yet another embodiment, the method further comprises adding an organic solvent to the first concentrated mixture and concentrating the resulting mixture under reduced pressure to remove residual water to form a second concentrated mixture. In yet another embodiment, the method further comprises adding an organic solvent to the first concentrated mixture or the second concentrated mixture, heating the resulting mixture to a temperature from about 40° C. to about 70° C., cooling the mixture to a temperature from about 0° C. to about 40° C., optionally adding seed crystals of (6R)-L-erythro-tetrahydrobiopterin dihydrochloride to the mixture to facilitate crystallization, and filtering the mixture to isolate (6R)-L-erythro-tetrahydrobiopterin dihydrochloride.

The process of the present disclosure can be used, and can be modified, to make any of the various polymorphic forms of tetrahydrobiopterin dihydrochloride known in the art, depending on the conditions used to crystallize tetrahydrobiopterin dihydrochloride. U.S. Application Publication 2006/0035900, which is incorporated herein by reference in its entirety, describes various polymorphic forms of tetrahydrobiopterin dihydrochloride and procedures for making those polymorphic forms. In an embodiment, the present process produces polymorph B of (6R)-L-erythro-tetrahydrobiopterin dihydrochloride. Polymorph B of (6R)-L-erythro-tetrahydrobiopterin dihydrochloride exhibits an X-ray powder diffraction (XRPD) pattern having peaks at, expressed in d-values (Å): 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w). The abbreviations in parentheses pertaining to the XRPD peaks have the following meaning: (vs)=very strong intensity, (s)=strong intensity, (m)=medium intensity, (w)=weak intensity, and (vw)=very weak intensity.

EXAMPLES

The following examples are provided merely for illustration and are not intended to limit the scope of the disclosure.

Example 1

Hydrolysis of Diacetylbiopterin Using a Phosphate Buffer

Hydrolysis of the two acetate esters of diacetylbiopterin (compound 9) was performed in a biphasic mixture of buffered water (pH about 11.8) and n-BuOH in eight separate runs. The same relative amounts of diacetylbiopterin, $Na_2HPO_4$, water, and n-BuOH were used in all of the eight experiments. Base (aqueous NaOH solution) was added to maintain the pH of the aqueous phase at about 11.8. The progress of the hydrolysis reaction was monitored by any of various analytical techniques known in the art (e.g., TLC, LC-MS, or HPLC). If the reaction mixture was warmed to about 35° C. and the pH of the aqueous phase was maintained at about 11.8 by continual monitoring and addition of base, the hydrolysis reaction could be completed in about 6 hours or less. Substantially complete hydrolysis of diacetylbiopterin was also accomplished by adjusting the pH of the aqueous phase about every 30 minutes for about 2 hours and then stirring the reaction mixture overnight at ambient temperature (about 25° C.). The desired product, biopterin, dissolved in the aqueous phase, and typically less than 0.5 g biopterin was lost to the organic phase starting with 50 g diacetylbiopterin.

After substantially complete hydrolysis of diacetylbiopterin, the reaction mixture was filtered through a celite plug and the water and n-BuOH layers were allowed to settle and separate. The aqueous layer was clear red-brown, while the organic layer was black due to dark colored organic impurities dissolved therein. The amounts of biopterin in the aqueous layer and the discarded organic layer were determined by HPLC, and are provided in Table 1.

TABLE 1

| Experiment | Diacetyl-biopterin (g) | Biopterin (g) in Aqu. Phase | Biopterin (g) in Org. Phase | Biopterin Yield (%) in Aqueous Phase |
|---|---|---|---|---|
| 1 | 50 | 36.6 | 0.20 | 103 |
| 2 | 50 | 31.8 | 0.25 | 90 |
| 3 | 50 | 30.7 | 0.46 | 87 |
| 4 | 50 | 36.1 | 0.30 | 102 |
| 5 | 40 | 24.3 | 0.28 | 86 |
| 6 | 50 | 31.6 | 0.40 | 89 |
| 7 | 50 | 32.7 | 0.34 | 93 |
| 8 | 40 | 26.2 | 0.23 | 93 |

The total biopterin yield in each of the eight hydrolysis experiments was high (at least 86%), and a very small amount of biopterin was lost to the discarded organic layer (less than about 1.3%), demonstrating the reproducibility of the procedure for the hydrolysis reaction. The aqueous layer containing biopterin was diluted to give the appropriate concentration of biopterin, and was used directly in the hydrogenation of biopterin.

Example 2

Lab-Scale Synthesis of Sapropterin Using Inorganic Bases and Buffer Diacetylbiopterin Hydrolysis in Buffered Aqueous Phase Followed by Phase Separation The following hydrolysis corresponds to Experiment No. 3 in Table 1. Diacetylbiopterin (about 50 g of diacetylbiopterin equivalent, 155 mmol (149 mmol corrected for purity)) and disodium hydrogen phosphate (11.0 g, 77.5 mmol) were slurried in a mixture of 1-butanol (125 mL) and water (200 mL). The mixture was warmed to 40° C., and aqueous sodium hydroxide solution (50 wt %) was added until the pH of the aqueous phase was approximately 11.8. The pH of the aqueous phase was checked and adjusted to pH about 11.8 about every 30 minutes for about 2 hours, and then the reaction mixture was stirred overnight at ambient temperature (about 25° C.). Then the reaction mixture was again warmed to 40° C., and the pH of the aqueous phase was adjusted to about 11.8 about every 30 minutes for about 1 hour. The mixture was filtered through a short celite pad (0.5 cm) in a sintered-glass funnel. The celite pad was washed with water (2×5 mL), and the filtrate was poured into a separatory funnel. After the aqueous and organic layers were allowed to settle and separate over a period of about 15 minutes, the aqueous layer containing biopterin was collected.

The concentrations of biopterin in the aqueous and organic layers were determined by HPLC. The aqueous layer was found to have a biopterin concentration of 109.7 mg/mL (30.7 g biopterin, 87% yield), while the organic layer contained 3.7 mg/mL of biopterin (0.46 g, 1.3%).

Hydrogenation of Biopterin in Buffered Solution to Form (6R)-BH4 Dihydrochloride $PtO_2$ (0.76 g, 3.3 mmol) was weighed into a 50 mL Büchi hydrogenation vessel, and water (25 mL) was added. The vessel was sealed and purged four times with nitrogen (0.5 bar). The vessel was pressurized with hydrogen (3.5 bar) to pre-hydrogenate the catalyst. The pressure was released after 2 minutes and the vessel was re-pressurized with hydrogen to 3.5 bar. The slurry was stirred with a magnetic stirrer at ambient temperature for 5 hours, while the hydrogen pressure was maintained at 3.5 bar. The pressure was released and the vessel was purged four times with nitrogen (0.5 bar).

The activated platinum catalyst was slurried into a 1 L Parr vessel, and the slurry in the hydrogenation vessel was rinsed into the Parr vessel with additional water (20 mL). The crude aqueous biopterin solution (30.7 g, 130 mmol, in 283 mL water) from the hydrolysis reaction above was added to the Parr vessel and the volume of the reaction was increased to 450 mL by addition of water. The pH of the mixture was adjusted to 11.9 by addition of either aqueous NaOH solution (50 wt %) or aqueous phosphoric acid solution (10%). The vessel was sealed and purged with nitrogen (6×7 bar), and the mixture was mechanically stirred (propeller shaft) at 400 rpm. The temperature of the reaction mixture was stabilized at 30° C. using internal heating coils and a water heater/circulator. After the final nitrogen purge was vented, the vessel was purged two times with hydrogen (to 7 bar) and then pressurized to 21 bar hydrogen with stirring at 600 rpm. After 5 minutes, the stirring was stopped, additional hydrogen was added to return the pressure to 21 bar, and stirring was resumed. This process was repeated every 15 minutes until, after two hours, hydrogen uptake had slowed to the point where the reactor pressure was maintained without addition of hydrogen. The mixture was stirred at 30° C. for 10 hours. The pressure was released and the vessel was immediately purged six times with nitrogen (7 bar). After the final purge, the vessel was vented and the mixture was transferred out of the vessel. The reaction mixture was filtered through a celite pad to remove the platinum catalyst, which was recovered, and the celite pad was washed with water. The combined filtrate was acidified with concentrated hydrochloric acid to give crude sapropterin dihydrochloride (about 80% yield by HPLC, 6R:6S ratio of about 7.6-8.1).

Figure 5:
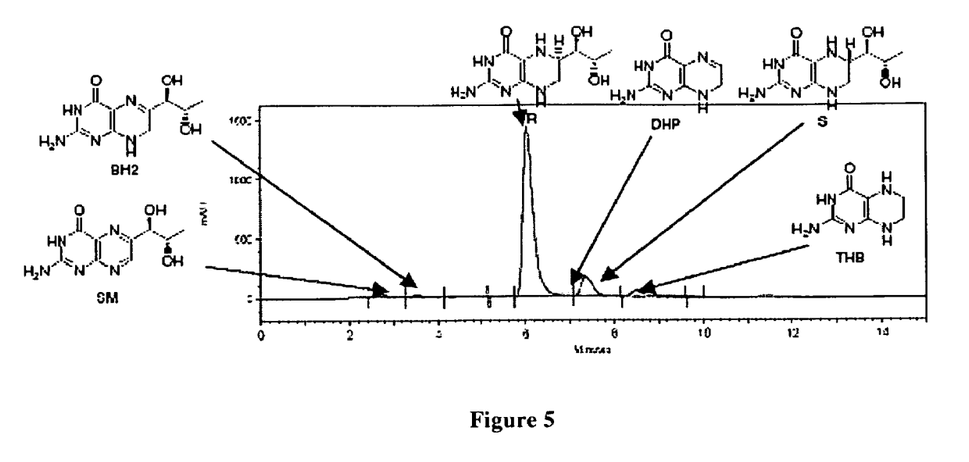
FIG. 5 is a chromatogram of the crude product of the biopterin hydrogenation reaction in Example 2, showing mostly (6R)-L-erythro-tetrahydrobiopterin and a small amount of the (6S)-diastereomer.

FIG. 5 is a chromatogram of the crude product of the hydrogenation reaction, and the peaks in the chromatogram are provided in Table 2. FIG. 5 and Table 2 show that the desired product, 6R-BH4 (peak no. 5), was the major product obtained in high yield (about 80%), and its diastereomer, 6S-BH4 (peak no. 6), was the only significant impurity.

TABLE 2

Detector Results, 1-265 nm (reprocessed)

| Peak Number | Retention Time | Area | Area Percent |
|---|---|---|---|
| 1 | 2.782 | 579060 | 2.01 |
| 2 | 3.508 | 433187 | 1.51 |
| 3 | 4.603 | 131869 | 0.46 |
| 4 | 5.415 | 82536 | 0.29 |
| 5 (6R-BH4) | 6.023 | 23416917 | 81.49 |
| 6 (6S-BH4) | 7.350 | 2951827 | 10.27 |
| 7 (tetrahydropterin) | 8.475 | 1138191 | 3.96 |
| 8 | 9.803 | 4067 | 0.01 |

Example 3

Lab-Scale Synthesis of Sapropterin Using Organic Amines

A. Hydrolysis of Diacetylbiopterin

To a mixture of diacetylbiopterin (about 50 g of diacetylbiopterin equivalent, 155 mmol) in 1-butanol (128 mL) at ambient temperature (20-25° C.) were added distilled water (200 mL) and diethylamine (26 g, 355 mmol). The mixture was stirred at 40° C. for 16 hrs, when the mixture contained ≦5% diacetylbiopterin a/a (area under the curve of chromatogram) by HPLC. The aqueous and organic phases were allowed to settle and separate without stirring, and the aqueous layer was collected. The organic layer was mixed with distilled water (160 mL) at 60° C. for 1 hr, the two phases were allowed to separate, and the aqueous layer was collected. The combined aqueous layers were filtered through Vitacel (2 g), and the filter cake was washed with distilled water (2×36 mL).

B. Hydrogenation of Biopterin

The combined aqueous solution containing biopterin from above was treated with triethylamine (136 mL) at 25° C. to adjust its pH to 11.2. The mixture was transferred to an autoclave, where a slurry of platinum black (1.2 g, 6 mmol) in distilled water (20 mL) was added to the mixture. After the resulting mixture was purged with nitrogen and hydrogen (3×2 bar nitrogen, 3×35 bar hydrogen), the mixture was stirred at 1,000 rpm at 25° C. under 35 bar hydrogen for 23 hrs, when the mixture contained ≦1% biopterin a/a and ≦8% 7,8-dihydrobiopterin a/a by HPLC. The mixture was purged with nitrogen and then filtered to remove the platinum catalyst. To increase the stability of tetrahydrobiopterin in solution, the pH of the filtrate solution was lowered to pH<1.0 by slow addition of 33% HCl (120 g, about 100 mL) at 25° C.

C. Isolation of "Crude" (6R)-Sapropterin Dihydrochloride

The above acidified aqueous solution containing crude (6R)-sapropterin dihydrochloride was concentrated via distillation under reduced pressure (50-200 mbar) and at 40-60° C. to remove about 375 g (375 mL) water (the distillation of water azeotroped away the acetic acid that was generated from the hydrolysis of diacetylbiopterin and subsequent acidification). Ethanol (58 mL) was added to the concentrated mixture, and the water content of the mixture was determined to be ≦23% w/w by the Karl-Fischer method. Additional ethanol (200 mL) was added to the mixture at 60° C., followed by 1-butanol (58 mL). The resulting mixture was stirred at 60° C. for 1 hr, cooled to 35° C., and stirred at 35° C. for 6 hrs to promote crystallization of "crude" (6R)-sapropterin dihydrochloride. The crystallized product was filtered and washed with ethanol (2×25 mL).

Example 4

Industrial-Scale Synthesis of Sapropterin Using Organic Amines

A. Hydrolysis of Diacetylbiopterin

Diacetylbiopterin (compound 9) (about 300 kg of diacetylbiopterin equivalent, 930 mol) was suspended in water (1320 kg, 1320 L) and 1-butanol (624 kg, 770 L). Diethylamine (156 kg, 2133 mol) was added, resulting in a mixture having a pH≧11.5, and the reaction mixture was stirred at 40° C. (for about 16 hrs) until the conversion to biopterin (compound 10) was at least 95% (i.e., the amount of monoacetylbiopterins and diacetylbiopterin totaled ≦5%). Water (240 kg, 240 L) then was added, the aqueous and organic phases were allowed to separate at 25° C. over a period of at least 30 min, and the two phases were split. Purified water (480 kg, 480 L) was added to the 1-butanol layer, the mixture was stirred well, the aqueous and organic phases were allowed to separate at 25° C. over a period of at least 60 min, and the two phases were split.

The combined aqueous layers were stirred with Vitacel FAC 200 (36 kg) (or a similar filter aid), the mixture was filtered, and the filter cake was washed with purified water (120 kg, 120 L). The concentration of biopterin in the filtrate was measured by HPLC, and was adjusted to 5.3% w/w with purified water. The residual amount of purified water used for slurrying platinum black (7.2 kg, 37 mol) and for rinsing the lines was calculated to result in a biopterin concentration of 4.8% w/w immediately before addition of triethylamine.

B. Hydrogenation of Biopterin

Triethylamine (447 kg, 4417 mol) was added to the above aqueous solution containing 4.8% w/w biopterin and platinum black (7.2 kg, 37 mol) at 0-5° C., resulting in a pH≧11.5. The mixture was stirred at 25° C. and under 50 bar $H_2$ (g) until the amount of biopterin was ≦1% a/a (area under the curve of chromatogram) and that of 7,8-dihydrobiopterin was ≦8% a/a (the mixture was stirred for about 23 hrs, but analysis of hydrogen uptake indicated that hydrogenation was substantially complete within 10 hrs). The mixture was filtered through a pad of celite to remove the platinum catalyst, the filter cake was washed with purified water (100 kg, 100 L), and the platinum catalyst was recovered for recycling. The filtrate was cooled to ≦15° C., and 32% hydrochloric acid (1646 kg, about 1371 L) was added to convert tetrahydrobiopterin to its more stable dihydrochloride salt in a low pH solution. The pH of the aqueous solution was checked to verify a pH value <1 at 2.5° C.±2.5.

C. Isolation of "Crude" (6R)-Sapropterin Dihydrochloride

The above aqueous solution containing crude (6R)-sapropterin dihydrochloride was concentrated via distillation under reduced pressure (≦200 mbar) and at $T_I$ (internal temperature of the solution)≦60° C., until the water content of the mixture by the Karl-Fischer method was between 30% and 36% w/w (the distillation of water azeotroped away the acetic acid that was generated from the hydrolysis of diacetylbiopterin and subsequent acidification). Hydrochloric acid (32%, about 160 kg, about 133 L) was added, and the solution was heated to 55° C. and then cooled to 35° C. and stirred at 35° C. for 1 hr. BH4 dihydrochloride started to crystallize at about 45° C., but the solution may be seeded with seed crystals of (6R)-BH4 dihydrochloride to induce crystallization. The resulting mixture was distilled under reduced pressure (≦200 mbar) and at $T_I$≦60° C. until its water content by Karl-Fischer was between 22% and 28% w/w. Ethanol (750 kg, 949 L) and 1-butanol (165 kg, 204 L) were added, and the mixture was stirred at 55° C. for 1 hr. The mixture was cooled to 35° C. to facilitate crystallization, the resulting crystallized product was filtered, and the filter cake was washed with ethanol (≧72 kg, 91 L).

D. Isolation of Pure (6R)-Sapropterin Dihydrochloride

The relatively "crude" (6R)-sapropterin dihydrochloride from above (about 320 kg wet product, corresponding to about 264 kg dried product) was dissolved in water (923 kg, 923 L). A slurry of activated charcoal L2S (17 kg) in water (170 kg, 170 L) was added, followed by Vitacel FAC 200 (40 kg) (or a similar filter aid), and the mixture was stirred at 25° C.±5 for at least 15 min and then filtered through a nutsch (suction filter) coated with moistened Vitacel FAC 200 (40 kg). The filter cake was washed with purified water (264 kg, 264 L). Hydrochloric acid (32%, 384 kg, about 320 L) was added to the clear yellowish filtrate, and a first portion of water (510 kg, 510 L) was distilled off under reduced pressure (≦200 mbar) at 30-60° C. 1-Butanol was added (538 kg, 664 L), and the mixture was distilled under reduced pressure (50-200 mbar) at 30-60° C. to azeotrope away water, until no further amount of water accumulated in the Dean-Stark trap (about 838 kg, 838 L). The water content of the mixture was measured by the Karl-Fischer method to ensure a value ≦11% w/w.

To crystallize (6R)-sapropterin dihydrochloride, absolute ethanol (1767 kg, 2237 L) was added to the above mixture, which was then heated to 55° C. The suspension was cooled to 35° C. over a period of at least 1 hr, and was stirred at 35° C. for an additional 3 hrs. The mixture was filtered, and the filter cake was washed twice with warm ethanol (35° C., 340 kg (430 L) in total). The filtered solid was dried at ≦60° C. for 3 to 48 hrs until loss on drying was ≦0.1% w/w, providing (6R)-L-erythro-sapropterin dihydrochloride (about 232 kg) of 99.8% purity.

It is understood that every embodiment or aspect of the disclosure described herein may optionally be combined with any one or more of the other embodiments or aspects described herein.

The foregoing description of the disclosure is merely provided to aid in its understanding, and modifications to the disclosure within its scope will be apparent to those having ordinary skill in the art.

The practice of the method disclosed herein, and individual steps thereof, can be performed manually and/or with the aid of electronic equipment. Although the method has been described with reference to particular embodiments, a person of ordinary skill in the art will readily appreciate that other ways of performing the acts and steps associated with the method may be used. For example, the order of the various steps may be changed without departing from the scope or spirit of the method, unless described otherwise. In addition, some of the individual steps can be combined, omitted, or further subdivided into additional steps.

All patents, publications and references cited herein are incorporated herein by reference in their entirety. In case of conflict between the present disclosure and incorporated patents, publications, and references, the present disclosure should control.

What is claimed is:

1. A method of preparing tetrahydrobiopterin, comprising: hydrolyzing diacetylbiopterin to biopterin in the presence of a base in a biphasic mixture, which comprises an aqueous phase containing water and an organic phase containing a water-immiscible organic solvent, wherein the aqueous phase has a pH of at least 10;
optionally allowing the aqueous phase and the organic phase to separate after the hydrolysis of diacetylbiopterin is substantially complete and optionally collecting the aqueous phase as an aqueous mixture; and
hydrogenating the biopterin in the aqueous mixture or the aqueous phase of the biphasic mixture, wherein the aqueous mixture or the aqueous phase has a pH of at least 10, to tetrahydrobiopterin in the presence of a platinum, palladium, or rhodium catalyst under a hydrogen pressure from 14 bar to 100 bar.

2. The method of claim 1, wherein the aqueous phase in the hydrolysis reaction has a pH of at least 11.

3. The method of claim 1, wherein the base in the hydrolysis reaction is an amine.

4. The method of claim 3, wherein the base is diethylamine.

5. The method of claim 1, wherein the water-immiscible organic solvent is an alcohol.

6. The method of claim 5, wherein the water-immiscible organic solvent is 1-butanol.

7. The method of claim 1, wherein the hydrolysis reaction is performed at a temperature from 20° C. to 50° C.

8. The method of claim 7, wherein the hydrolysis reaction is performed at 40° C.

9. The method of claim 1, wherein the concentration of diacetylbiopterin in the aqueous phase is from 150 mg/mL to 300 mg/mL.

10. The method of claim 1, comprising allowing the aqueous phase and the organic phase to separate after the hydrolysis of diacetylbiopterin is substantially complete and collecting the aqueous phase as an aqueous mixture.

11. The method of claim 10, further comprising adding a base to the collected aqueous phase to raise the pH of the resulting aqueous mixture to at least 10.

12. The method of claim 11, wherein the pH of the aqueous mixture is raised to at least 11.

13. The method of claim 11, wherein the base added to the collected aqueous phase is an amine.

14. The method of claim 13, wherein the base is triethylamine.

15. The method of claim 1, wherein the hydrogen pressure is from 20 bar to 50 bar.

16. The method of claim 15, wherein the hydrogen pressure is 50 bar.

17. The method of claim 1, wherein the metal catalyst is a platinum catalyst.

18. The method of claim 17, wherein the metal catalyst is platinum black.

19. The method of claim 1, wherein the amount of the metal catalyst is from 2 mol % to 8 mol % based on the amount of diacetylbiopterin prior to hydrolyzing diacetylbiopterin or based on the amount of biopterin prior to hydrogenating biopterin.

20. The method of claim 1, wherein the hydrogenation is performed at a temperature from 0° C. to 40° C.

21. The method of claim 1, wherein the hydrogenation is performed at a temperature from 20° C. to 30° C.

22. The method of claim 1, where the concentration of biopterin in the aqueous mixture in the hydrogenation is from 2% w/w to 8% w/w.

23. The method of claim 1, wherein tetrahydrobiopterin is formed in a 6R:6S diastereomeric ratio of at least 7.

24. The method of claim 1, further comprising, after the hydrogenation of biopterin is substantially complete, filtering the aqueous mixture to remove the metal catalyst, and adding hydrochloric acid to the filtered aqueous mixture to lower the pH of the mixture to no greater than 3 to form (6R)-L-erythro-tetrahydrobiopterin dihydrochloride.

25. The method of claim 24, wherein the pH of the filtered aqueous mixture is lowered to no greater than 1.

26. A method of preparing (6R)-L-erythro-tetrahydrobiopterin dihydrochloride in a crystalline form designated polymorph B, which exhibits a characteristic X-ray powder diffraction pattern with characteristic peaks expressed in d-values (Å): 8.7 (vs), 6.9 (w), 5.90 (vw), 5.63 (m), 5.07 (m), 4.76 (m), 4.40 (m), 4.15 (w), 4.00 (s), 395 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (m), 2.84 (s), 2.82 (m), 2.69 (w), 2.59 (w), and 2.44 (w); comprising:

hydrolyzing diacetylbiopterin to biopterin in the presence of a base in a biphasic mixture, which comprises an aqueous phase containing water and an organic phase containing a water-immiscible organic solvent, wherein the aqueous phase has a pH of at least 10;

optionally allowing the aqueous phase and the organic phase to separate after the hydrolysis of diacetylbiopterin is substantially complete and optionally collecting the aqueous phase as an aqueous mixture;

hydrogenating the biopterin in the aqueous mixture or the aqueous phase of the biphasic mixture, wherein the aqueous mixture or the aqueous phase has a pH of at least 10, to tetrahydrobiopterin in the presence of a platinum, palladium, or rhodium catalyst under a hydrogen pressure from 14 bar to 100 bar; and after the hydrogenation of biopterin is substantially complete, filtering the aqueous mixture to remove the metal catalyst, and adding hydrochloric acid to the filtered aqueous mixture to lower the pH of the mixture to no greater than 3 to form (6R)-L-erythro-tetrahydrobiopterin dihydrochloride polymorph B.

* * * * *

UNITED STATES PATENT AND TRADEMARK OFFICE
CERTIFICATE OF CORRECTION

PATENT NO.        : 8,178,670 B2
APPLICATION NO.   : 12/349479
DATED             : May 15, 2012
INVENTOR(S)       : Mark Henderson et al.

Page 1 of 1

It is certified that error appears in the above-identified patent and that said Letters Patent is hereby corrected as shown below:

In the Claims

In claim 26, column 25, line 6, replace "395 (m)" with --"3.95 (m)"--.

Signed and Sealed this
Fourteenth Day of January, 2014

Michelle K. Lee
*Deputy Director of the United States Patent and Trademark Office*